(12) United States Patent
Larsen et al.

(10) Patent No.: US 11,130,793 B2
(45) Date of Patent: Sep. 28, 2021

(54) GLP-1/GLP-2 DUAL AGONISTS

(71) Applicant: Zealand Pharma A/S, Glostrup (DK)

(72) Inventors: Bjarne Due Larsen, Roskilde (DK);
Lise Giehm, Frederiksberg (DK);
Alistair Vincent Gordon Edwards,
Copenhagen S (DK)

(73) Assignee: Zealand Pharma A/S, Søborg (DK)

( * ) Notice: Subject to any disclaimer, the term of this patent is extended or adjusted under 35 U.S.C. 154(b) by 48 days.

(21) Appl. No.: 16/466,930

(22) PCT Filed: Dec. 11, 2017

(86) PCT No.: PCT/EP2017/082289
§ 371 (c)(1),
(2) Date: Jun. 5, 2019

(87) PCT Pub. No.: WO2018/104560
PCT Pub. Date: Jun. 14, 2018

(65) Prior Publication Data
US 2019/0338009 A1    Nov. 7, 2019

(30) Foreign Application Priority Data
Dec. 9, 2016   (DK) .............................. PA201600756

(51) Int. Cl.
| | |
|---|---|
| *C07K 14/605* | (2006.01) |
| *A61P 3/10* | (2006.01) |
| *A61P 1/00* | (2006.01) |
| *A61K 38/00* | (2006.01) |

(52) U.S. Cl.
CPC .............. *C07K 14/605* (2013.01); *A61P 1/00* (2018.01); *A61P 3/10* (2018.01); *A61K 38/00* (2013.01)

(58) Field of Classification Search
CPC ......... C07K 14/605; A61K 38/00; A61P 1/00; A61P 3/10
See application file for complete search history.

(56) References Cited

U.S. PATENT DOCUMENTS

2007/0117752 A1 * 5/2007 Larsen ................... A61K 47/26
514/11.7

FOREIGN PATENT DOCUMENTS

| EA | 020497 B1 | 11/2014 |
|---|---|---|
| WO | WO-98/08871 A1 | 3/1998 |
| WO | WO-98/11125 A1 | 3/1998 |
| WO | WO-2006/117565 A2 | 11/2006 |
| WO | WO-2011/143335 A2 | 11/2011 |
| WO | WO-2013/164484 A1 | 11/2013 |
| WO | WO-2016/066818 A1 | 5/2016 |

OTHER PUBLICATIONS

DaCambra et al., "Structural determinants for activity of glucagon-like peptide-2," Biochemistry. 39(30):8888-94 (2000).
International Preliminary Report on Patentability for International Application No. PCT/EP2017/082289, dated Jun. 11, 2019 (6 pages).
International Search Report and Written Opinion for International Application No. PCT/EP2017/082289, dated Mar. 23, 2018 (10 pages).
Altschul et al., "Local alignment statistics," Methods Enzymol. 266:460-480 (1996).
Benjamin et al., "Glucagon-like peptide-2 enhances intestinal epithelial barrier function of both transcellular and paracellular pathways in the mouse," Gut. 47(1):112-9 (2000).
Brun et al., "Increased intestinal permeability in obese mice: new evidence in the pathogenesis of nonalcoholic steatohepatitis," Am J Physiol Gastrointest Liver Physiol. 292(2):G518-25 (2007).
Cani et al., "Changes in gut microbiota control inflammation in obese mice through a mechanism involving GLP-2-driven improvement of gut permeability," Gut. 58(8): 1091-1103 (2009).
Cani et al., "Changes in gut microbiota control metabolic endotoxemia-induced inflammation in high-fat diet-induced obesity and diabetes in mice," Diabetes. 57(6):1470-81 (2008).
Cheeseman, "Upregulation of SGLT-1 transport activity in rat jejunum induced by GLP-2 infusion in vivo," Am J Physiol. 273(6 Pt 2):R1965-71 (1997).
Drucker et al., "Induction of intestinal epithelial proliferation by glucagon-like peptide 2," Proc Nat Acad Sci U.S.A. 93(15):7911-6 (1996).
Fields et al., Principles and practice of solid-phase peptide synthesis. *Synthetic Peptides: A User's Guide (Second Edition).* ed. Gregory A. Grant, Oxford University Press, Inc., 93-219 (2002).
Guan et al., "GLP-2-mediated up-regulation of intestinal blood flow and glucose uptake is nitric oxide-dependent in TPN-fed piglets," Gastroenterology. 125(1):136-47 (2003).
Hadjiyanni et al., "Glucagon-like peptide-2 reduces intestinal permeability but does not modify the onset of type 1 diabetes in the nonobese diabetic mouse," Endocrinology. 150(2):592-9 (2009).
Hellström et al., "GLP-1 suppresses gastrointestinal motility and inhibits the migrating motor complex in healthy subjects and patients with irritable bowel syndrome," Neurogastroenterol Motil. 20(6):649-59 (2008).
Holst, "The physiology of glucagon-like peptide 1," Physiol Rev. 87(4): 1409-39 (2007).
Kim et al., "The role of incretins in glucose homeostasis and diabetes treatment," Pharmacol Rev. 60(4):470-512 (2008).

(Continued)

*Primary Examiner* — Li N Komatsu

(74) *Attorney, Agent, or Firm* — Clark & Elbing LLP

(57) ABSTRACT

The invention relates to compounds having agonist activity at the GLP-1 (glucagon-like-peptide 1) and GLP-2 (glucagon-like peptide 2) receptors. The compounds find use, inter alia, in the prophylaxis or treatment of intestinal damage and dysfunction, regulation of body weight, and prophylaxis or treatment of metabolic dysfunction.

19 Claims, No Drawings
Specification includes a Sequence Listing.

(56) References Cited

OTHER PUBLICATIONS

Pearson et al., "Comparison of DNA sequences with protein sequences," Genomics. 46(1): 24-36 (1997).
Sinclair et al., "Proglucagon-derived peptides: mechanisms of action and therapeutic potential," Physiology (Bethesda). 20:357-65 (2005).
Tolessa et al., "Glucagon-like peptide-1 retards gastric emptying and small bowel transit in the rat: effect mediated through central or enteric nervous mechanisms," Dig Dis Sci. 43(10):2284-90 (1998).
Wøjdemann et al., "Inhibition of sham feeding-stimulated human gastric acid secretion by glucagon-like peptide-2," J Clin Endocrinol Metab. 84(7):2513-7 (1999).

* cited by examiner

GLP-1/GLP-2 DUAL AGONISTS

RELATED APPLICATION

The present application is a national phase application under U.S.C. § 371 of International Application No. PCT/EP2017/082289 filed Dec. 11, 2017, which claims priority from Danish Application No. PA201600756 filed on Dec. 9, 2016, both of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 26, 2021 is named 50412-112001_Sequence_Listing_3_26_21_ST25 and is 80,541 bytes in size. No new matter has been added.

FIELD OF THE INVENTION

The present invention relates to compounds having agonist activity at the GLP-1 (glucagon-like-peptide 1) and GLP-2 (glucagon-like peptide 2) receptors. The compounds find use, inter alia, in the prophylaxis or treatment of intestinal damage and dysfunction, regulation of body weight, and prophylaxis or treatment of metabolic dysfunction.

BACKGROUND TO THE INVENTION

Intestinal tissue is responsible for the production of both human glucagon-like peptide 1 (GLP-1(7-36)) and human glucagon-like peptide 2 (GLP-2 (1-33)) as they are produced by the same cells. Human GLP-2 is a 33-amino-acid peptide with the following sequence: Hy-His-Ala-Asp-Gly-Ser-Phe-Ser-Asp-Glu-Met-Asn-Thr-Ile-Leu-Asp-Asn-Leu-Ala-Ala-Arg-Asp-Phelle-Asn-Trp-Leu-Ile-Gln-Thr-Lys-Ile-Thr-Asp-OH (SEQ ID NO: 1). It is derived from specific posttranslational processing of proglucagon in the enteroendocrine L cells of the intestine and in specific regions of the brainstem. GLP-2 binds to a single G-protein-coupled receptor belonging to the class II glucagon secretin family. GLP-2 is co-secreted with GLP-1, oxyntomodulin and glicentin, in response to nutrient ingestion. Human GLP-1 is produced as a 30-amino acid peptide with the following sequence: Hy-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ (SEQ ID NO: 2).

GLP-2 has been reported to induce significant growth of the small intestinal mucosal epithelium via the stimulation of stem cell proliferation in the crypts, and by inhibition of apoptosis in the villi (Drucker et al., 1996, Proc. Natl. Acad. Sci. USA 93: 7911-7916). GLP-2 also has growth effects on the colon. Furthermore, GLP-2 inhibits gastric emptying and gastric acid secretion (Wojdemann et al., 1999, J. Clin. Endocrinol. Metab. 84: 2513-2517), enhances intestinal barrier function (Benjamin et al., 2000, Gut 47: 112-119), stimulates intestinal hexose transport via the upregulation of glucose transporters (Cheeseman, 1997, Am. J. Physiol. R1965-71), and increases intestinal blood flow (Guan et al., 2003, Gastroenterology, 125: 136-147).

GLP-1 has been described as a physiological incretin hormone and has thus been mostly reported to augment an insulin response after an oral intake of glucose or fat. It is, however, generally understood that GLP-1 lowers glucagon concentrations, has beneficial effects on inhibition of fast bowel movements (Tolessa et al., 1998, Dig. Dis. Sci. 43(10): 2284-90), and slows gastric emptying.

WO2013/164484 discloses GLP-2 analogues which comprise one or more substitutions compared to h[Gly2]GLP-2 and which may have the property of an altered GLP-1 activity, and their medical use.

WO2016/066818 describes peptides having dual agonist activity at the GLP-1 and GLP-2 receptors, and proposes medical uses thereof. However, there remains a need for further compounds which combine effective agonist activities at both receptors with acceptable levels of stability.

SUMMARY OF THE INVENTION

Broadly, the present invention relates to compounds which have agonist activity at the GLP-1 (glucagon-like peptide 1) and GLP-2 (glucagon-like peptide 2) receptors, e.g. as assessed in in vitro potency assays. Such compounds are referred to in this specification as "GLP-1/GLP-2 dual agonists", or simply "dual agonists". Thus, the compounds of the present invention have activities of both GLP-1 (7-36) and GLP-2 (1-33).

The invention provides a GLP-1/GLP-2 dual agonist represented by the formula:

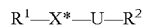

wherein:
R$^1$ is hydrogen (Hy), C$_{1-4}$ alkyl (e.g. methyl), acetyl, formyl, benzoyl or trifluoroacetyl;
R$^2$ is NH$_2$ or OH;
X* is a peptide of formula I:

(I)
```
                                              (SEQ ID NO: 3)
H-X2-EG-X5-F-X7-X8-E-X10-X11-TIL-X15-X16-X17-A-
X19-X20-X21-FI-X24-WL-X27-X28-X29-KIT-X33
``` wherein:
X2 is Aib or G;
X5 is S or T;
X7 is S or T;
X8 is S, E or D;
X10 is L, M or V;
X11 is A, N or S;
X15 is D or E;
X16 is E, A or G;
X17 is Q, E, L or K;
X19 is A, V or S;
X20 is R or K;
X21 is D, L or E;
X24 is A, N or S;
X27 is I, Y, Q, H or K;
X28 is A, E, H, Y, L, K, Q, R or S;
X29 is H, Y, K or Q;
X33 is D or E;
U is absent or a sequence of 1-15 residues, each independently selected from K and k;
and wherein at least one of X5 and X7 is T;
or a pharmaceutically acceptable salt or solvate thereof.

The various amino acid positions in peptide X* of the formulae provided here are numbered according to their linear position from N- to C-terminus in the amino acid chain.

Dual agonists having aspartic acid (Asp, D) at position 3 and glycine (Gly) in position 4 can be very potent agonists at the GLP-1 and GLP-2 receptors. However, this combination of substitutions results in compounds which are unstable and may not be suitable for long term storage in aqueous solution. Without wishing to be bound by theory, it is believed that the Asp at position 3 may isomerise to iso-Asp via a cyclic intermediate formed between the carboxylic acid functional group of its side chain and the backbone nitrogen atom of the residue at position 4.

It has now been found that molecules having glutamic acid (Glu, E) at position 3 instead of Asp are much less susceptible to such reactions and hence may be considerably more stable when stored in aqueous solution. However, replacement of Asp with Glu at position 3 may reduce the potency at one or both of the GLP-2 receptor and the GLP-1 receptor, even though Glu is present at position 3 of the native GLP-1 molecule. Simultaneously incorporating a Thr residue at one or both of positions 5 and 7 appears to compensate for some or all of the lost potency, especially in combination with incorporation of His (H), Tyr (Y) or Gln (Q) at position 29 instead of the Gly (G) and Thr (T) residues present in wild type human GLP-1 and 2 respectively.

In some embodiments of formula I:
X2 is Aib;
X5 is S or T;
X7 is S or T;
X8 is S or D;
X10 is L;
X11 is A or S;
X15 is D or E;
X16 is E or G;
X17 is Q or K;
X19 is A or S;
X20 is R;
X21 is D or E;
X24 is A, N or S;
X27 is I, Y, Q or K;
X28 is A, E, H, Y or L;
X29 is H, Y or Q; and
X33 is D.

In some embodiments, X2 is Aib.
In some embodiments, X8 is S.
In some embodiments, X7 is T.
In some embodiments, X5 is T.
In some embodiments, X29 is H.
In some embodiments, X27 is I.
In some embodiments, X27 is Q and X29 is Q.
In some embodiments, X28 is A and X29 is H.
In some embodiments, X28 is E and X29 is H.
In some embodiments, X11 is A.
In some embodiments X16 is E and X17 is Q. In some embodiments, X16 is G and X17 is K.

If X* contains any of X11 is S, X15 is E, X19 is S, or X21 is E, it may contain two, three or all four of those residues. For example:
X11 is S and X15 is E;
X11 is S and X19 is S;
X11 is S and X21 is E;
X15 is E and X19 is S;
X15 is E and X21 is E;
X11 is S, X15 is E and X19 is S;
X11 is S, X15 is E and X21 is E;
X11 is S, X19 is S and X21 is E;
X15 is E, X19 is S and X21 is E; or
X11 is S, X15 is E, X19 is S and X21 is E.

In some embodiments, the residues X8-X24 contain a maximum of four changes compared to the sequence SELA-TILDEQAARDFIA (SEQ ID NO: 4), e.g. a maximum of three, a maximum of two, or a maximum of one change compared to that sequence.

In some embodiments, X27 may be I. For example, X27 is I and X28 is A.

In some embodiments, the residues at X27-X29 have a sequence selected from:
IAH;
HAH;
QAH;
YAH;
IAQ;
IAY;
YEH;
IQH;
IKH;
IRH;
ISH;
HQH;
QAQ;
HAQ;
YAH;
YRH;
KAH;
KSY;
KEQ;
IEH; and
ILH.

In some embodiments, X* is a peptide of formula II:

(II)
(SEQ ID NO: 5)
H[Aib]EG-X5-F-X7-SELATILDEQAARDFIAWLI-X28-X29-KITD wherein
X5 is S or T;
X7 is S or T;
X28 is A, E, H, Y or L;
X29 is H, Y or Q;
and wherein at least one of X5 and X7 is T.

In any of the formulae or embodiments described above, the dual agonist contains one of the following combinations of residues:
X5 is S and X7 is T;
X5 is T and X7 is S;
X5 is T and X7 is T.

It may be preferred that X5 is S and X7 is T, or X5 is T and X7 is T.

X29 may be H, Y or Q, and in some embodiments is H.

When present, U represents a peptide sequence of 1-15 lysine residues, e.g. 1-10 lysine residues. Each of the amino acid residues in the peptide sequence U may have either D-configuration (designated "k") or L-configuration (designated "K"). In certain embodiments, all have an L-configuration or all D-configuration. Examples include a peptide sequence of 1-15 lysine residues, 1-10 lysine residues and 1-7 lysine residues, e.g., 3 lysine residues, 4 lysine residues, 5 lysine residues, 6 lysine residues and 7 lysine residues, especially 5 lysine residues and 6 lysine residues. Exemplary peptides containing U may have the sequence:
H-X2-EG-X5-F-X7-X8-E-X10-X11-TIL-X15-X16-X17-A-X19-X20-X21-FI-X24-WL-X27-X28-X29-KIT-X33-K
(SEQ ID NO: 47);
H-X2-EG-X5-F-X7-X8-E-X10-X11-TIL-X15-X16-X17-A-X19-X20-X21-FI-X24-WL-X27-X28-X29-KIT-X33-K-K
(SEQ ID NO: 48);

H-X2-EG-X5-F-X7-X8-E-X10-X11-TIL-X15-X16-X17-A-X19-X20-X21-FI-X24-WL-X27-X28-X29-KIT-X33-K-K-K (SEQ ID NO: 49);
H-X2-EG-X5-F-X7-X8-E-X10-X11-TIL-X15-X16-X17-A-X19-X20-X21-FI-X24-W L-X27-X28-X29-KIT-X33-K-K-K-K (SEQ ID NO: 50);
H-X2-EG-X5-F-X7-X8-E-X10-X11-TIL-X15-X16-X17-A-X19-X20-X21-FI-X24-WL-X27-X28-X29-KIT-X33-K-K-K-K-K (SEQ ID NO: 51);
H-X2-EG-X5-F-X7-X8-E-X10-X11-TIL-X15-X16-X17-A-X19-X20-X21-FI-X24-WL-X27-X28-X29-KIT-X33-K-K-K-K-K-K (SEQ ID NO: 52);
H-X2-EG-X5-F-X7-X8-E-X10-X11-TIL-X15-X16-X17-A-X19-X20-X21-FI-X24-WL-X27-X28-X29-KIT-X33-K-K-K-K-K-K-K (SEQ ID NO: 53);
H-X2-EG-X5-F-X7-X8-E-X10-X11-TIL-X15-X16-X17-A-X19-X20-X21-FI-X24-WL-X27-X28-X29-KIT-X33-K-K-K-K-K-K-K-K (SEQ ID NO: 54);
H-X2-EG-X5-F-X7-X8-E-X10-X11-TIL-X15-X16-X17-A-X19-X20-X21-FI-X24-WL-X27-X28-X29-KIT-X33-K-K-K-K-K-K-K-K-K (SEQ ID NO: 55);
H-X2-EG-X5-F-X7-X8-E-X10-X11-TIL-X15-X16-X17-A-X19-X20-X21-FI-X24-WL-X27-X28-X29-KIT-X33-K-K-K-K-K-K-K-K-K-K (SEQ ID NO: 56);
H-X2-EG-X5-F-X7-X8-E-X10-X11-TIL-X15-X16-X17-A-X19-X20-X21-FI-X24-WL-X27-X28-X29-KIT-X33-K-K-K-K-K-K-K-K-K-K-K (SEQ ID NO: 57);
H-X2-EG-X5-F-X7-X8-E-X10-X11-TIL-X15-X16-X17-A-X19-X20-X21-FI-X24-W L-X27-X28-X29-KIT-X33-K-K-K-K-K-K-K-K-K-K-K (SEQ ID NO: 58);
H-X2-EG-X5-F-X7-X8-E-X10-X11-TIL-X15-X16-X17-A-X19-X20-X21-FI-X24-WL-X27-X28-X29-KIT-X33-K-K-K-K-K-K-K-K-K-K-K-K (SEQ ID NO: 59);
H-X2-EG-X5-F-X7-X8-E-X10-X11-TIL-X15-X16-X17-A-X19-X20-X21-FI-X24-WL-X27-X28-X29-KIT-X33-K-K-K-K-K-K-K-K-K-K-K-K-K (SEQ ID NO: 60);
H-X2-EG-X5-F-X7-X8-E-X10-X11-TIL-X15-X16-X17-A-X19-X20-X21-FI-X24-WL-X27-X28-X29-KIT-X33-K-K-K-K-K-K-K-K-K-K-K-K-K-K (SEQ ID NO: 61);
H-X2-EG-X5-F-X7-X8-E-X10-X11-TIL-X15-X16-X17-A-X19-X20-X21-FI-X24-WL-X27-X28-X29-KIT-X33-k (SEQ ID NO: 62);
H-X2-EG-X5-F-X7-X8-E-X10-X11-TIL-X15-X16-X17-A-X19-X20-X21-FI-X24-W L-X27-X28-X29-KIT-X33-k-k (SEQ ID NO: 63);
H-X2-EG-X5-F-X7-X8-E-X10-X11-TIL-X15-X16-X17-A-X19-X20-X21-FI-X24-WL-X27-X28-X29-KIT-X33-k-k-k (SEQ ID NO: 64);
H-X2-EG-X5-F-X7-X8-E-X10-X11-TIL-X15-X16-X17-A-X19-X20-X21-FI-X24-WL-X27-X28-X29-KIT-X33-k-k-k-k (SEQ ID NO: 65);
H-X2-EG-X5-F-X7-X8-E-X10-X11-TIL-X15-X16-X17-A-X19-X20-X21-FI-X24-WL-X27-X28-X29-KIT-X33-k-k-k-k-k (SEQ ID NO: 66);
H-X2-EG-X5-F-X7-X8-E-X10-X11-TIL-X15-X16-X17-A-X19-X20-X21-FI-X24-WL-X27-X28-X29-KIT-X33-k-k-k-k-k-k (SEQ ID NO: 67);
H-X2-EG-X5-F-X7-X8-E-X10-X11-TIL-X15-X16-X17-A-X19-X20-X21-FI-X24-W L-X27-X28-X29-KIT-X33-k-k-k-k-k-k-k (SEQ ID NO: 68);
H-X2-EG-X5-F-X7-X8-E-X10-X11-TIL-X15-X16-X17-A-X19-X20-X21-FI-X24-WL-X27-X28-X29-KIT-X33-k-k-k-k-k-k-k-k (SEQ ID NO: 69);
H-X2-EG-X5-F-X7-X8-E-X10-X11-TIL-X15-X16-X17-A-X19-X20-X21-FI-X24-WL-X27-X28-X29-KIT-X33-k-k-k-k-k-k-k-k (SEQ ID NO: 70);
H-X2-EG-X5-F-X7-X8-E-X10-X11-TIL-X15-X16-X17-A-X19-X20-X21-FI-X24-WL-X27-X28-X29-KIT-X33-k-k-k-k-k-k-k-k-k (SEQ ID NO: 71);
H-X2-EG-X5-F-X7-X8-E-X10-X11-TIL-X15-X16-X17-A-X19-X20-X21-FI-X24-WL-X27-X28-X29-KIT-X33-k-k-k-k-k-k-k-k-k-k (SEQ ID NO: 72);
H-X2-EG-X5-F-X7-X8-E-X10-X11-TIL-X15-X16-X17-A-X19-X20-X21-FI-X24-WL-X27-X28-X29-KIT-X33-k-k-k-k-k-k-k-k-k-k (SEQ ID NO: 73);
H-X2-EG-X5-F-X7-X8-E-X10-X11-TIL-X15-X16-X17-A-X19-X20-X21-FI-X24-WL-X27-X28-X29-KIT-X33-k-k-k-k-k-k-k-k-k-k-k (SEQ ID NO: 74);
H-X2-EG-X5-F-X7-X8-E-X10-X11-TIL-X15-X16-X17-A-X19-X20-X21-FI-X24-WL-X27-X28-X29-KIT-X33-k-k-k-k-k-k-k-k-k-k-k-k (SEQ ID NO: 75);
H-X2-EG-X5-F-X7-X8-E-X10-X11-TIL-X15-X16-X17-A-X19-X20-X21-FI-X24-WL-X27-X28-X29-KIT-X33-k-k-k-k-k-k-k-k-k-k-k-k-k (SEQ ID NO: 76);

wherein:
X2 is Aib or G;
X5 is S or T;
X7 is S or T;
X8 is S, E or D;
X10 is L, M or V;
X11 is A, N or S;
X15 is D or E;
X16 is E, A or G;
X17 is Q, E, L or K;
X19 is A, V or S;
X20 is R or K;
X21 is D, L or E;
X24 is A, N or S;
X27 is I, Y, Q, H or K;
X28 is A, E, H, Y, L, K, Q, R or S;
X29 is H, Y, K or Q;
X33 is D or E;
and wherein at least one of X5 and X7 is T;
or a pharmaceutically acceptable salt or solvate thereof.

In certain embodiments, U is absent.
In some embodiments R¹ is Hy and/or R² is OH.
The peptide X* may have the sequence:

```
                                          (SEQ ID NO: 6)
H[Aib]EGSFTSELATILDEQAARDFIAWLIAHKITD;

(SEQ ID NO: 7)
H[Aib]EGTFSSELATILDEQAARDFIAWLIAHKITD;

(SEQ ID NO: 8)
H[Aib]EGTFTSELATILDEQAARDFIAWLIAHKITD;

(SEQ ID NO: 9)
H[Aib]EGSFTSELATILDEQAARDFIAWLIEHKITD;

(SEQ ID NO: 10)
H[Aib]EGTFTSELATILDEQAARDFIAWLIEHKITD;

(SEQ ID NO: 11)
H[Aib]EGSFTSELATILDEQAARDFIAWLIHHKITD;

(SEQ ID NO: 12)
H[Aib]EGSFTSELATILDEQAARDFIAWLIYHKITD;

(SEQ ID NO: 13)
H[Aib]EGSFTSELATILDEQAARDFIAWLILHKITD;

(SEQ ID NO: 14)
H[Aib]EGTFTDELATILDEQAARDFIAWLIAHKITD;
```

```
                                          (SEQ ID NO: 15)
H[Aib]EGTFTSELSTILDEQAARDFIAWLIAHKITD;

(SEQ ID NO: 16)
H[Aib]EGTFTSELATILDGKAARDFIAWLIAHKITD;

(SEQ ID NO: 17)
H[Aib]EGTFTSELATILDEQAARDFIAWLHAHKITD;

(SEQ ID NO: 18)
H[Aib]EGTFTSELATILDEQAARDFIAWLQAHKITD;

(SEQ ID NO: 19)
H[Aib]EGTFTSELATILDEQAARDFIAWLYAHKITD;

(SEQ ID NO: 20)
H[Aib]EGTFTSELATILDEQAARDFIAWLIQHKITD;

(SEQ ID NO: 21)
H[Aib]EGTFTSELATILDEQAARDFIAWLIKHKITD;

(SEQ ID NO: 22)
H[Aib]EGTFTSELATILDEQAARDFIAWLIRHKITD;

(SEQ ID NO: 23)
H[Aib]EGTFTSELATILDEQAARDFIAWLISHKITD;

(SEQ ID NO: 24)
H[Aib]EGTFTSELATILDEQAARDFIAWLIAQKITD;

(SEQ ID NO: 25)
H[Aib]EGTFTSELATILDEQAARDFIAWLIAYKITD;

(SEQ ID NO: 26)
H[Aib]EGTFTSELATILDEQAARDFIAWLHQHKITD;

(SEQ ID NO: 27)
H[Aib]EGSFTSELATILDEQAARDFIAWLHAHKITD;

(SEQ ID NO: 28)
H[Aib]EGSFTSELATILDEQAARDFIAWLYEHKITD;

(SEQ ID NO: 29)
H[Aib]EGSFTSELATILDEQAARDFIAWLQAHKITD;

(SEQ ID NO: 30)
H[Aib]EGSFTSELATILDEQAARDFIAWLIAQKITD;

(SEQ ID NO: 31)
H[Aib]EGTFTSELATILDEQAARDFIAWLQAQKITD;

(SEQ ID NO: 32)
H[Aib]EGTFTSELSTILDEQAARDFIAWLHAQKITD;

(SEQ ID NO: 33)
H[Aib]EGSFTSELATILDEQAARDFIAWLYAHKITD;

(SEQ ID NO: 34)
H[Aib]EGTFTDELATILDEQAARDFIAWLQAQKITD;

(SEQ ID NO: 35)
H[Aib]EGSFTSELATILDEQAARDFIAWLYRHKITD;

(SEQ ID NO: 36)
H[Aib]EGSFTSELATILDGKAARDFIAWLIAHKITD;

(SEQ ID NO: 37)
H[Aib]EGTFSSELATILDGKAARDFIAWLIAHKITD;

(SEQ ID NO: 38)
H[Aib]EGTFTSELATILDEQAARDFINWLIAHKITD;

(SEQ ID NO: 39)
H[Aib]EGTFTSELATILDEQAARDFISWLIAHKITD;

(SEQ ID NO: 40)
H[Aib]EGTFTSELATILDEQAARDFINWLKAHKITD;

(SEQ ID NO: 41)
H[Aib]EGTFTSELATILDEQAARDFINWLKSYKITD;

(SEQ ID NO: 42)
H[Aib]EGTFTSELATILDEQAARDFINWLKEQKITD;

(SEQ ID NO: 43)
HGEGTFTSELATILDEQAARDFIAWLIAHKITD;

(SEQ ID NO: 44)
H[Aib]EGTFSSELSTILEEQASREFIAWLIAHKITE;

(SEQ ID NO: 45)
HGEGSFSSELATILDEQAARDFIAWLIQHKITD;
or (SEQ ID NO: 46)
H[Aib]EGSFSSELATILDEQAARDFIAWLIQHKITD.
```

The dual agonist may be:

```
(Compound 1, SEQ ID NO: 6)
Hy-H[Aib]EGSFTSELATILDEQAARDFIAWLIAHKITD-OH;

(Compound 2, SEQ ID NO: 7)
Hy-H[Aib]EGTFSSELATILDEQAARDFIAWLIAHKITD-OH;

(Compound 3, SEQ ID NO: 8)
Hy-H[Aib]EGTFTSELATILDEQAARDFIAWLIAHKITD-OH;

(Compound 4, SEQ ID NO: 9)
Hy-H[Aib]EGSFTSELATILDEQAARDFIAWLIEHKITD-OH;

(Compound 5, SEQ ID NO: 10)
Hy-H[Aib]EGTFTSELATILDEQAARDFIAWLIEHKITD-OH;

(Compound 6, SEQ ID NO: 11)
Hy-H[Aib]EGSFTSELATILDEQAARDFIAWLIHHKITD-OH;

(Compound 7, SEQ ID NO: 12)
Hy-H[Aib]EGSFTSELATILDEQAARDFIAWLIYHKITD-OH;

(Compound 8, SEQ ID NO: 13)
Hy-H[Aib]EGSFTSELATILDEQAARDFIAWLILHKITD-OH;

(Compound 9, SEQ ID NO: 14)
Hy-H[Aib]EGTFTDELATILDEQAARDFIAWLIAHKITD-OH;

(Compound 10, SEQ ID NO: 15)
Hy-H[Aib]EGTFTSELSTILDEQAARDFIAWLIAHKITD-OH;

(Compound 11, SEQ ID NO: 16)
Hy-H[Aib]EGTFTSELATILDGKAARDFIAWLIAHKITD-OH;

(Compound 12, SEQ ID NO: 17)
Hy-H[Aib]EGTFTSELATILDEQAARDFIAWLHAHKITD-OH;

(Compound 13, SEQ ID NO: 18)
Hy-H[Aib]EGTFTSELATILDEQAARDFIAWLQAHKITD-OH;

(Compound 14, SEQ ID NO: 19)
Hy-H[Aib]EGTFTSELATILDEQAARDFIAWLYAHKITD-OH;

(Compound 15, SEQ ID NO: 20)
Hy-H[Aib]EGTFTSELATILDEQAARDFIAWLIQHKITD-OH;

(Compound 16, SEQ ID NO: 21)
Hy-H[Aib]EGTFTSELATILDEQAARDFIAWLIKHKITD-OH;

(Compound 17, SEQ ID NO: 22)
Hy-H[Aib]EGTFTSELATILDEQAARDFIAWLIRHKITD-OH;

(Compound 18, SEQ ID NO: 23)
Hy-H[Aib]EGTFTSELATILDEQAARDFIAWLISHKITD-OH;

(Compound 19, SEQ ID NO: 24)
Hy-H[Aib]EGTFTSELATILDEQAARDFIAWLIAQKITD-OH;

(Compound 20, SEQ ID NO: 25)
Hy-H[Aib]EGTFTSELATILDEQAARDFIAWLIAYKITD-OH;
```

-continued (Compound 21, SEQ ID NO: 26)
Hy-H[Aib]EGTFTSELATILDEQAARDFIAWLHQHKITD-OH;

(Compound 22, SEQ ID NO: 27)
Hy-H[Aib]EGSFTSELATILDEQAARDFIAWLHAHKITD-OH;

(Compound 23, SEQ ID NO: 28)
Hy-H[Aib]EGSFTSELATILDEQAARDFIAWLYEHKITD-OH;

(Compound 24, SEQ ID NO: 29)
Hy-H[Aib]EGSFTSELATILDEQAARDFIAWLQAHKITD-OH;

(Compound 25, SEQ ID NO: 30)
Hy-H[Aib]EGSFTSELATILDEQAARDFIAWLIAQKITD-OH;

(Compound 26, SEQ ID NO: 31)
Hy-H[Aib]EGTFTSELATILDEQAARDFIAWLQAQKITD-OH;

(Compound 27, SEQ ID NO: 32)
Hy-H[Aib]EGTFTSELSTILDEQAARDFIAWLHAQKITD-OH;

(Compound 28, SEQ ID NO: 33)
Hy-H[Aib]EGSFTSELATILDEQAARDFIAWLYAHKITD-OH;

(Compound 29, SEQ ID NO: 34)
Hy-H[Aib]EGTFTDELATILDEQAARDFIAWLQAQKITD-OH;

(Compound 30, SEQ ID NO: 35)
Hy-H[Aib]EGSFTSELATILDEQAARDFIAWLYRHKITD-OH;

(Compound 31, SEQ ID NO: 36)
Hy-H[Aib]EGSFTSELATILDGKAARDFIAWLIAHKITD-OH;

(Compound 32, SEQ ID NO: 37)
Hy-H[Aib]EGTFSSELATILDGKAARDFIAWLIAHKITD-OH;

(Compound 33, SEQ ID NO: 38)
Hy-H[Aib]EGTFTSELATILDEQAARDFINWLIAHKITD-OH;

(Compound 34, SEQ ID NO: 39)
Hy-H[Aib]EGTFTSELATILDEQAARDFISWLIAHKITD-OH;

(Compound 35, SEQ ID NO: 40)
Hy-H[Aib]EGTFTSELATILDEQAARDFINWLKAHKITD-OH;

(Compound 36, SEQ ID NO: 41)
Hy-H[Aib]EGTFTSELATILDEQAARDFINWLKSYKITD-OH;

(Compound 37, SEQ ID NO: 42)
Hy-H[Aib]EGTFTSELATILDEQAARDFINWLKEQKITD-OH;

(Compound 38, SEQ ID NO: 43)
Hy-HGEGTFTSELATILDEQAARDFIAWLIAHKITD-OH;

(Compound 39, SEQ ID NO: 44)
Hy-H[Aib]EGTFSSELSTILEEQASREFIAWLIAHKITE-OH;

(Compound 40, SEQ ID NO: 45)
Hy-HGEGSFSSELATILDEQAARDFIAWLIQHKITD-[NH2];
or (Compound 41, SEQ ID NO: 46)
Hy-H[Aib]EGSFSSELATILDEQAARDFIAWLIQHKITD-OH.

The dual agonist may be in the form of a pharmaceutically acceptable salt or solvate, such as a pharmaceutically acceptable acid addition salt.

The invention also provides a composition comprising a dual agonist of the invention, or a pharmaceutically acceptable salt or solvate thereof, together with a carrier, excipient or vehicle. The carrier may be a pharmaceutically acceptable carrier.

The composition may be a pharmaceutical composition. The pharmaceutical composition may be formulated as a liquid suitable for administration by injection or infusion. It may be formulated to achieve slow release of the dual agonist.

The present invention further provides a dual agonist of the invention for use in therapy. In yet another aspect there is provided a dual agonist of the present invention for use as a medicament. Also provided is a dual agonist of the invention for use in a method of medical treatment.

The invention also provides a dual agonist of the invention for use in a method of increasing intestinal mass, improving intestinal function (especially intestinal barrier function), increasing intestinal blood flow, or repairing intestinal damage or dysfunction, e.g. damage to the intestinal epithelium.

The invention also provides a dual agonist of the invention for use in a method of prophylaxis or treatment of malabsorption, ulcers (e.g. peptic ulcers, Zollinger-Ellison Syndrome, drug-induced ulcers, and ulcers related to infections or other pathogens), short-bowel syndrome, cul-de-sac syndrome, inflammatory bowel disease (Crohns disease and ulcerative colitis), irritable bowel syndrome (IBS), pouchitis, celiac sprue (for example arising from gluten induced enteropathy or celiac disease), tropical sprue, hypogammaglobulinemic sprue, mucositis induced by chemotherapy or radiation therapy, diarrhea induced by chemotherapy or radiation therapy, low grade inflammation, metabolic endotoxemia, necrotising enterocolitis, primary biliary cirrhosis, hepatitis, fatty liver disease (including parental nutrition associated gut atrophy, PNALD (Parenteral Nutrition-Associated Liver Disease), NAFLD (Non-Alcoholic Fatty Liver Disease) and NASH (Non-Alcoholic Steatohepatitis)), or gastrointestinal side-effects of inflammatory conditions such as pancreatitis or graft versus host disease (GVHD).

The invention also provides a dual agonist of the invention for use in a method of reducing or inhibiting weight gain, reducing gastric emptying or intestinal transit, reducing food intake, reducing appetite, or promoting weight loss.

The invention also provides a dual agonist of the invention for use in a method of prophylaxis or treatment of obesity, morbid obesity, obesity-linked gallbladder disease, obesity-induced sleep apnea, inadequate glucose control, glucose tolerance, dyslipidaemia (e.g. elevated LDL levels or reduced HDL/LDL ratio), diabetes (e.g. Type 2 diabetes, gestational diabetes), pre-diabetes, metabolic syndrome or hypertension.

The invention also provides a method of increasing intestinal mass, improving intestinal function (especially intestinal barrier function), increasing intestinal blood flow, or repairing intestinal damage or dysfunction in a subject in need thereof, the method comprising administering a dual agonist of the invention to the subject.

The invention also provides a method of prophylaxis or treatment of malabsorption, ulcers (e.g. peptic ulcers, Zollinger-Ellison Syndrome, drug-induced ulcers, and ulcers related to infections or other pathogens), short-bowel syndrome, cul-de-sac syndrome, inflammatory bowel disease (Crohns disease and ulcerative colitis), irritable bowel syndrome (IBS), pouchitis, celiac sprue (for example arising from gluten induced enteropathy or celiac disease), tropical sprue, hypogammaglobulinemic sprue, mucositis induced by chemotherapy or radiation therapy, diarrhea induced by chemotherapy or radiation therapy, low grade inflammation, metabolic endotoxemia, necrotising enterocolitis, primary biliary cirrhosis, hepatitis, fatty liver disease (including parental nutrition associated gut atrophy, PNALD (Parenteral Nutrition-Associated Liver Disease), NAFLD (Non-Alcoholic Fatty Liver Disease) and NASH (Non-Alcoholic Steatohepatitis)), or gastrointestinal side-effects of inflammatory conditions such as pancreatitis or graft versus host disease (GVHD) in a subject in need thereof, the method comprising administering a dual agonist of the invention to the subject.

The invention also provides a method of reducing or inhibiting weight gain, reducing gastric emptying or intestinal transit, reducing food intake, reducing appetite, or promoting weight loss in a subject in need thereof, the method comprising administering a dual agonist of the invention to the subject.

The invention also provides a method of prophylaxis or treatment of obesity, morbid obesity, obesity-linked gallbladder disease, obesity-induced sleep apnea, inadequate glucose control, glucose tolerance, dyslipidaemia (e.g. elevated LDL levels or reduced HDL/LDL ratio), diabetes (e.g. Type 2 diabetes, gestational diabetes), pre-diabetes, metabolic syndrome or hypertension in a subject in need thereof, the method comprising administering a dual agonist of the invention to the subject.

The invention also provides the use of a dual agonist of the invention in the preparation of a medicament for increasing intestinal mass, improving intestinal function (especially intestinal barrier function), increasing intestinal blood flow, or repairing intestinal damage or dysfunction, e.g. damage to the intestinal epithelium.

The invention also provides the use of a dual agonist of the invention in the preparation of a medicament for prophylaxis or treatment of malabsorption, ulcers (e.g. peptic ulcers, Zollinger-Ellison Syndrome, drug-induced ulcers, and ulcers related to infections or other pathogens), short-bowel syndrome, cul-de-sac syndrome, inflammatory bowel disease (Crohns disease and ulcerative colitis), irritable bowel syndrome (IBS), pouchitis, celiac sprue (for example arising from gluten induced enteropathy or celiac disease), tropical sprue, hypogammaglobulinemic sprue, mucositis induced by chemotherapy or radiation therapy, diarrhea induced by chemotherapy or radiation therapy, low grade inflammation, metabolic endotoxemia, necrotising enterocolitis, primary biliary cirrhosis, hepatitis, fatty liver disease (including parental nutrition associated gut atrophy, PNALD (Parenteral Nutrition-Associated Liver Disease), NAFLD (Non-Alcoholic Fatty Liver Disease) and NASH (Non-Alcoholic Steatohepatitis)), or gastrointestinal side-effects of inflammatory conditions such as pancreatitis or graft versus host disease (GVHD).

The invention also provides the use of a dual agonist of the invention in the preparation of a medicament for reducing or inhibiting weight gain, reducing gastric emptying or intestinal transit, reducing food intake, reducing appetite, or promoting weight loss.

The invention also provides the use of a dual agonist of the invention in the preparation of a medicament for prophylaxis or treatment of obesity, morbid obesity, obesity-linked gallbladder disease, obesity-induced sleep apnea, inadequate glucose control, glucose tolerance, dyslipidaemia (e.g. elevated LDL levels or reduced HDL/LDL ratio), diabetes (e.g. Type 2 diabetes, gestational diabetes), pre-diabetes, metabolic syndrome or hypertension.

A further aspect provides a therapeutic kit comprising a dual agonist, or a pharmaceutically acceptable salt or solvate thereof, according to the invention.

DETAILED DESCRIPTION OF THE INVENTION

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

All patents, published patent applications and non-patent publications referred to in this application are specifically incorporated by reference herein. In case of conflict, the present specification, including its specific definitions, will control.

Each embodiment of the invention described herein may be taken alone or in combination with one or more other embodiments of the invention.

Definitions

Unless specified otherwise, the following definitions are provided for specific terms which are used in the present written description.

Throughout this specification, the word "comprise", and grammatical variants thereof, such as "comprises" or "comprising", will be understood to imply the inclusion of a stated integer or component, or group of integers or components, but not the exclusion of any other integer or component, or group of integers or components.

The singular forms "a," "an," and "the" include the plurals unless the context clearly dictates otherwise.

The term "including" is used to mean "including but not limited to". "Including" and "including but not limited to" may be used interchangeably.

The terms "patient", "subject" and "individual" may be used interchangeably and refer to either a human or a non-human animal. These terms include mammals such as humans, primates, livestock animals (e.g., bovines and porcines), companion animals (e.g., canines and felines) and rodents (e.g., mice and rats).

The term "solvate" in the context of the present invention refers to a complex of defined stoichiometry formed between a solute (in casu, a peptide or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

The term "agonist" as employed in the context of the invention refers to a substance (ligand) that activates the receptor type in question.

Throughout the present description and claims the conventional three-letter and one-letter codes for naturally occurring amino acids are used, i.e.
A (Ala), G (Gly), L (Leu), I (Ile), V (Val), F (Phe), W (Trp), S (Ser), T (Thr), Y (Tyr), N (Asn), Q (Gln), D (Asp), E (Glu), K (Lys), R (Arg), H (His), M (Met), C (Cys) and P (Pro); as well as generally accepted three-letter codes for other a-amino acids, such as sarcosine (Sar), norleucine (Nle), α-aminoisobutyric acid (Aib), 2,3-diaminopropanoic acid (Dap), 2,4-diaminobutanoic acid (Dab) and 2,5-diaminopentanoic acid (ornithine; Orn). Such other a-amino acids may be shown in square brackets "[ ]" (e.g. "[Aib]") when used in a general formula or sequence in the present specification, especially when the rest of the formula or sequence is shown using the single letter code. Unless otherwise specified, amino acid residues in peptides of the invention are of the L-configuration. However, D-configuration amino acids may be incorporated. In the present context, an amino acid code written with a small letter represents the D-configuration of said amino acid, e.g. "k" represents the D-configuration of lysine (K).

Among sequences disclosed herein are sequences incorporating a "Hy-"moiety at the amino terminus (N-terminus)

of the sequence, and either an "—OH" moiety or an "—NH$_2$" moiety at the carboxy terminus (C-terminus) of the sequence. In such cases, and unless otherwise indicated, a "Hy-" moiety at the N-terminus of the sequence in question indicates a hydrogen atom [i.e. R$^1$=hydrogen=Hy in the general formulas; corresponding to the presence of a free primary or secondary amino group at the N-terminus], while an "—OH" or an "—NH$_2$" moiety at the C-terminus of the sequence indicates a hydroxy group [e.g. R$^2$=OH in general formulas; corresponding to the presence of a carboxy (COOH) group at the C-terminus] or an amino group [e.g. R$^2$=[NH$_2$] in the general formulas; corresponding to the presence of an amido (CONH$_2$) group at the C-terminus], respectively. In each sequence of the invention, a C-terminal "—OH" moiety may be substituted for a C-terminal "—NH$_2$" moiety, and vice-versa.

"Percent (%) amino acid sequence identity" with respect to the GLP-2 polypeptide sequences is defined as the percentage of amino acid residues in a candidate sequence that are identical to the amino acid residues in the wild-type (human) GLP-2 sequence, after aligning the sequences and introducing gaps, if necessary, to achieve the maximum percent sequence identity, and not considering any conservative substitutions as part of the sequence identity. Sequence alignment can be carried out by the skilled person using techniques well known in the art, for example using publicly available software such as BLAST, BLAST2 or Align software. For examples, see Altschul et al., Methods in Enzymology 266: 460-480 (1996) or Pearson et al., Genomics 46: 24-36, 1997.

The percentage sequence identities used herein in the context of the present invention may be determined using these programs with their default settings. More generally, the skilled worker can readily determine appropriate parameters for determining alignment, including any algorithms needed to achieve maximal alignment over the full length of the sequences being compared.

Dual Agonist Compounds

In accordance with the present invention, the dual agonist has at least one GLP-1 and at least one GLP-2 biological activity. Exemplary GLP-1 physiological activities include reducing rate of intestinal transit, reducing rate of gastric emptying, reducing appetite, food intake or body weight, and improving glucose control and glucose tolerance. Exemplary GLP-2 physiological activities include causing an increase in intestinal mass (e.g. of small intestine or colon), intestinal repair, and improving intestinal barrier function (i.e. reducing permeability of the intestine). These parameters can be assessed in in vivo assays in which the mass and the permeability of the intestine, or a portion thereof, is determined after a test animal has been treated with a dual agonist.

The dual agonists have agonist activity at the GLP-1 and GLP-2 receptors, e.g. the human GLP-1 and GLP-2 receptors. EC$_{50}$ values for in vitro receptor agonist activity may be used as a numerical measure of agonist potency at a given receptor. An EC$_{50}$ value is a measure of the concentration (e.g. mol/L) of a compound required to achieve half of that compound's maximal activity in a particular assay. A compound having a numerical EC$_{50}$ at a particular receptor which is lower than the EC$_{50}$ of a reference compound in the same assay may be considered to have higher potency at that receptor than the reference compound.

GLP-1 Activity

In some embodiments, the dual agonist has an EC$_{50}$ at the GLP-1 receptor (e.g. the human GLP-1 receptor) which is below 2.0 nM, below 1.5 nM, below 1.0 nM, below 0.9 nM, below 0.8 nM, below 0.7 nM, below 0.6 nM, below 0.5 nM, below 0.4 nM, below 0.3 nM, below 0.2 nM, below 0.1 nM, below 0.09 nM, below 0.08 nM, below 0.07 nM, below 0.06 nM, below 0.05 nM, below 0.04 nM, e.g. when assessed using the GLP-1 receptor potency assay described in the Examples below.

In some embodiments, the dual agonist has an EC$_{50}$ at the GLP-1 receptor which is between 0.001 nM and 1.0 nM, between 0.001 nM and 0.5 nM, or between 0.001 nM and 0.1 nM, e.g. when assessed using the GLP-1 receptor potency assay described in the Examples below.

An alternative measure of GLP-1 agonist activity may be derived by comparing the potency of a dual agonist with the potency of a known (or reference) GLP-1 agonist when both are measured in the same assay. Thus the relative potency at the GLP-1 receptor may be defined as:

$$[EC_{50}(\text{reference agonist})]/[EC_{50}(\text{dual agonist})].$$

Thus a value of 1 indicates that the dual agonist and reference agonist have equal potency, a value of >1 indicates that the dual agonist has higher potency (i.e. lower EC$_{50}$) than the reference agonist, and a value of <1 indicates that the dual agonist has lower potency (i.e. higher EC$_{50}$) than the reference agonist.

The reference GLP-1 agonist may, for example, be human GLP-1(7-37), liraglutide (NN2211; Victoza), or Exendin-4, but is preferably liraglutide.

Typically the relative potency will be between 0.001 and 100, e.g.

between 0.001 and 10, between 0.001 and 5, between 0.001 and 1, between 0.001 and 0.5, between 0.001 and 0.1, between 0.001 and 0.05, or between 0.001 and 0.01;

between 0.01 and 10, between 0.01 and 5, between 0.01 and 1, between 0.01 and 0.5, between 0.01 and 0.1, or between 0.01 and 0.05;

between 0.05 and 10, between 0.05 and 5, between 0.05 and 1, between 0.05 and 0.5, or between 0.05 and 0.1;

between 0.1 and 10, between 0.1 and 5, between 0.1 and 1, or between 0.1 and 0.5;

between 0.5 and 10, between 0.5 and 5, or between 0.5 and 1;

between 1 and 10, or between 1 and 5;

or between 5 and 10.

The present dual agonists have comparable GLP-1 potency to liraglutide. Thus the relative potency may particularly be between 0.5 and 10, between 0.5 and 5, between 0.5 and 1, between 1 and 10, or between 1 and 5.

By contrast, the dual agonists of the invention have higher potency at the GLP-1 receptor (e.g. the human GLP-1 receptor) than wild type human GLP-2 (hGLP-2 (1-33)) or [Gly2]-hGLP-2 (1-33) (i.e. human GLP-2 having glycine at position 2, also known as teduglutide). Thus, the relative potency of the dual agonists at the GLP-1 receptor compared to hGLP-2 (1-33) or teduglutide is greater than 1, typically greater than 5 or greater than 10, and may be up to 100, up to 500, or even higher.

GLP-2 Activity

In some embodiments, the dual agonist has an EC$_{50}$ at the GLP-2 receptor (e.g. the human GLP-2 receptor) which is below 2.0 nM, below 1.5 nM, below 1.0 nM, below 0.9 nM, below 0.8 nM, below 0.7 nM, below 0.6 nM, below 0.5 nM, below 0.4 nM, below 0.3 nM, below 0.2 nM, below 0.1 nM, below 0.09 nM, below 0.08 nM, below 0.07 nM, below 0.06 nM, below 0.05 nM, below 0.04 nM, below 0.03 nM, below 0.02 nM, or below 0.01 nM, e.g. when assessed using the GLP-1 receptor potency assay described in the Examples below.

In some embodiments, the dual agonist has an $EC_{50}$ at the GLP-2 receptor which is between 0.001 nM and 1.0 nM, between 0.001 nM and 0.5 nM, or between 0.001 nM and 0.25 nM,
e.g. between 0.01 nM and 1.0 nM, between 0.01 nM and 0.5 nM, or between 0.01 nM and 0.25 nM, e.g. when assessed using the GLP-2 receptor potency assay described in the Examples below.

An alternative measure of GLP-2 agonist activity may be derived by comparing the potency of a dual agonist with the potency of a known (or reference) GLP-2 agonist when both are measured in the same assay. Thus the relative potency at the GLP-2 receptor may be defined as:

$$[EC_{50}(\text{reference agonist})]/[EC_{50}(\text{dual agonist})].$$

Thus a value of 1 indicates that the dual agonist and reference agonist have equal potency, a value of >1 indicates that the dual agonist has higher potency (i.e. lower $EC_{50}$) than the reference agonist, and a value of <1 indicates that the dual agonist has lower potency (i.e. higher $EC_{50}$) than the reference agonist.

The reference GLP-2 agonist may, for example, be human GLP-2(1-33) or teduglutide ([Gly2]-hGLP-2 (1-33)), but is preferably teduglutide. Typically the relative potency will be between 0.001 and 100, e.g.
between 0.001 and 10, between 0.001 and 5, between 0.001 and 1, between 0.001 and 0.5, between 0.001 and 0.25, between 0.001 and 0.1, between 0.001 and 0.05, or between 0.001 and 0.01;
between 0.01 and 10, between 0.01 and 5, between 0.01 and 1, between 0.01 and 0.5, between 0.01 and 0.25, between 0.01 and 0.1, or between 0.01 and 0.05;
between 0.05 and 10, between 0.05 and 5, between 0.05 and 1, between 0.05 and 0.5, between 0.05 and 0.25, or between 0.05 and 0.1;
between 0.1 and 10, between 0.1 and 5, between 0.1 and 1, between 0.1 and 0.5, or between 0.1 and 0.25;
between 0.25 and 10, between 0.25 and 5, between 0.25 and 1 or between 0.25 and 0.5;
between 0.5 and 10, between 0.5 and 5, or between 0.5 and 1;
between 1 and 10, or between 1 and 5;
or between 5 and 10.

The GLP-2 potency of the present dual agonists is comparable to, or slightly lower than, teduglutide. Thus the relative potency may particularly be between 0.1 and 1, between 0.1 and 0.5, or between 0.1 and 0.25, between 0.25 and 1, or between 0.25 and 0.5;

By contrast, the dual agonists of the invention have higher potency at the GLP-2 receptor (e.g. the human GLP-2 receptor) than human GLP-1(7-37), liraglutide (NN2211; Victoza), or Exendin-4. Thus, the relative potency of the dual agonists at the GLP-2 receptor compared to human GLP-1(7-37), liraglutide (NN2211; Victoza), or Exendin-4 is greater than 1, typically greater than 5 or greater than 10, and may be up to 100, up to 500, or even higher (if the reference GLP-1 agonist even exerts detectable activity at the GLP-2 receptor).

It will be understood that the absolute potencies of the dual agonists at each receptor are much less important than the balance between the GLP-1 and GLP-2 agonist activities. Thus it is perfectly acceptable for the absolute GLP-1 or GLP-2 potency to be lower than that of known agonists at those receptors, as long as the dual agonist compound exerts acceptable relative levels of potency at both receptors. Any apparent deficiency in absolute potency can be compensated by an increased dose if required.

Synthesis of Dual Agonists

It is preferred to synthesize dual agonists of the invention by means of solid-phase or liquid-phase peptide synthesis methodology. In this context, reference may be made to WO 98/11125 and, among many others, Fields, G. B. et al., 2002, "Principles and practice of solid-phase peptide synthesis". In: Synthetic Peptides (2nd Edition), and the Examples herein.

In accordance with the present invention, a dual agonist of the invention may be synthesized or produced in a number of ways, including for example, a method which comprises (a) synthesizing the dual agonist by means of solid-phase or liquid-phase peptide synthesis methodology and recovering the synthesized dual agonist thus obtained; or
(b) expressing a precursor peptide sequence from a nucleic acid construct that encodes the precursor peptide, recovering the expression product, and modifying the precursor peptide to yield a compound of the invention.

The precursor peptide may be modified by introduction of one or more non-proteinogenic amino acids (e.g. Aib), introduction of the appropriate terminal groups R1 and R2, etc.

Expression is typically performed from a nucleic acid encoding the precursor peptide, which may be performed in a cell or a cell-free expression system comprising such a nucleic acid.

It is preferred to synthesize the analogues of the invention by means of solid-phase or liquid-phase peptide synthesis. In this context, reference is made to WO 98/11125 and, among many others, Fields, G B et al., 2002, "Principles and practice of solid-phase peptide synthesis". In: Synthetic Peptides (2nd Edition), and the Examples herein.

For recombinant expression, the nucleic acid fragments encoding the precursor peptide will normally be inserted in suitable vectors to form cloning or expression vectors. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) are capable of autonomous replication, thereby enabling high copy-numbers for the purposes of high-level expression or high-level replication for subsequent cloning.

In general outline, an expression vector comprises the following features in the 5'→3' direction and in operable linkage: a promoter for driving expression of the nucleic acid fragment, optionally a nucleic acid sequence encoding a leader peptide enabling secretion (to the extracellular phase or, where applicable, into the periplasma), the nucleic acid fragment encoding the precursor peptide, and optionally a nucleic acid sequence encoding a terminator. They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The vectors of the invention are used to transform host cells to produce the precursor peptide. Such transformed cells can be cultured cells or cell lines used for propagation of the nucleic acid fragments and vectors, and/or used for recombinant production of the precursor peptides.

Preferred transformed cells are micro-organisms such as bacteria [such as the species *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (e.g., *Saccharomyces cerevisiae* and *Pichia pastoris*), and protozoans. Alternatively, the transformed cells may be derived from a multicellular organism, i.e. it may be fungal cell, an insect cell, an algal cell, a plant cell, or an animal cell such as a mammalian cell. For the purposes of cloning and/or optimised expression it is preferred that the transformed cell is capable of replicating the nucleic acid fragment of the invention. Cells expressing the nucleic fragment can be used for small-scale or large-scale preparation of the peptides of the invention.

When producing the precursor peptide by means of transformed cells, it is convenient, although far from essential, that the expression product is secreted into the culture medium.

Pharmaceutical Compositions and Administration

An aspect of the present invention relates to a composition comprising a dual agonist according to the invention, or a pharmaceutically acceptable salt or solvate thereof, together with a carrier. In one embodiment of the invention, the composition is a pharmaceutical composition and the carrier is a pharmaceutically acceptable carrier. The present invention also relates to a pharmaceutical composition comprising a dual agonist according to the invention, or a salt or solvate thereof, together with a carrier, excipient or vehicle. Accordingly, the dual agonist of the present invention, or salts or solvates thereof, especially pharmaceutically acceptable salts or solvates thereof, may be formulated as compositions or pharmaceutical compositions prepared for storage or administration, and which comprise a therapeutically effective amount of a dual agonist of the present invention, or a salt or solvate thereof.

Suitable salts formed with bases include metal salts, such as alkali metal or alkaline earth metal salts, for example sodium, potassium or magnesium salts; ammonia salts and organic amine salts, such as those formed with morpholine, thiomorpholine, piperidine, pyrrolidine, a lower mono-, di- or tri-alkylamine (e.g., ethyl-tert-butyl-, diethyl-, diisopropyl-, triethyl-, tributyl- or dimethylpropylamine), or a lower mono-, di- or tri-(hydroxyalkyl)amine (e.g., mono-, di- or triethanolamine). Internal salts may also be formed. Similarly, when a compound of the present invention contains a basic moiety, salts can be formed using organic or inorganic acids. For example, salts can be formed from the following acids: formic, acetic, propionic, butyric, valeric, caproic, oxalic, lactic, citric, tartaric, succinic, fumaric, maleic, malonic, mandelic, malic, phthalic, hydrochloric, hydrobromic, phosphoric, nitric, sulphuric, benzoic, carbonic, uric, methanesulphonic, naphthalenesulphonic, benzenesulphonic, toluenesulphonic, p-toluenesulphonic (i.e. 4-methylbenzene-sulphonic), camphorsulphonic, 2-aminoethanesulphonic, aminomethylphosphonic and trifluoromethanesulphonic acid (the latter also being denoted triflic acid), as well as other known pharmaceutically acceptable acids. Amino acid addition salts can also be formed with amino acids, such as lysine, glycine, or phenylalanine.

In one embodiment, a pharmaceutical composition of the invention is one wherein the dual agonist is in the form of a pharmaceutically acceptable acid addition salt.

As will be apparent to one skilled in the medical art, a "therapeutically effective amount" of a dual agonist compound or pharmaceutical composition thereof of the present invention will vary depending upon, inter alia, the age, weight and/or gender of the subject (patient) to be treated. Other factors that may be of relevance include the physical characteristics of the specific patient under consideration, the patient's diet, the nature of any concurrent medication, the particular compound(s) employed, the particular mode of administration, the desired pharmacological effect(s) and the particular therapeutic indication. Because these factors and their relationship in determining this amount are well known in the medical arts, the determination of therapeutically effective dosage levels, the amount necessary to achieve the desired result of treating and/or preventing and/or remedying malabsorption and/or low-grade inflammation described herein, as well as other medical indications disclosed herein, will be within the ambit of the skilled person.

As used herein, the term "a therapeutically effective amount" refers to an amount which reduces symptoms of a given condition or pathology, and preferably which normalizes physiological responses in an individual with that condition or pathology. Reduction of symptoms or normalization of physiological responses can be determined using methods routine in the art and may vary with a given condition or pathology. In one aspect, a therapeutically effective amount of one or more dual agonists, or pharmaceutical compositions thereof, is an amount which restores a measurable physiological parameter to substantially the same value (preferably to within 30%, more preferably to within 20%, and still more preferably to within 10% of the value) of the parameter in an individual without the condition or pathology in question.

In one embodiment of the invention, administration of a compound or pharmaceutical composition of the present invention is commenced at lower dosage levels, with dosage levels being increased until the desired effect of preventing/treating the relevant medical indication is achieved. This would define a therapeutically effective amount. For the dual agonists of the present invention, alone or as part of a pharmaceutical composition, such human doses of the active dual agonist may be between about 0.01 pmol/kg and 500 µmol/kg body weight, between about 0.01 pmol/kg and 300 µmol/kg body weight, between 0.01 pmol/kg and 100 µmol/kg body weight, between 0.1 pmol/kg and 50 µmol/kg body weight, between 1 pmol/kg and 10 µmol/kg body weight, between 5 pmol/kg and 5 µmol/kg body weight, between 10 pmol/kg and 1 µmol/kg body weight, between 50 pmol/kg and 0.1 µmol/kg body weight, between 100 pmol/kg and 0.01 µmol/kg body weight, between 0.001 µmol/kg and 0.5 µmol/kg body weight, between 0.05 µmol/kg and 0.1 µmol/kg body weight.

The therapeutic dosing and regimen most appropriate for patient treatment will of course vary with the disease or condition to be treated, and according to the patient's weight and other parameters. Without wishing to be bound by any particular theory, it is expected that doses, in the µg/kg range, and shorter or longer duration or frequency of treatment may produce therapeutically useful results, such as a statistically significant increase particularly in small bowel mass. In some instances, the therapeutic regimen may include the administration of maintenance doses appropriate for preventing tissue regression that occurs following cessation of initial treatment. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

Medical Conditions

In a broad aspect, the present invention provides a dual agonist of the invention for use as a medicament.

In a further aspect, the present invention relates to a dual agonist of the invention for use in therapy.

The dual agonists described in this specification have biological activities of both GLP-1 and GLP-2.

GLP-2 induces significant growth of the small intestinal mucosal epithelium via the stimulation of stem cell proliferation in the crypts and inhibition of apoptosis on the villi (Drucker et al. Proc Natl Acad Sci USA. 1996, 93:7911-6). GLP-2 also has growth effects on the colon. GLP-2 also inhibits gastric emptying and gastric acid secretion (Wojdemann et al. J Clin Endocrinol Metab. 1999, 84:2513-7), enhances intestinal barrier function (Benjamin et al. Gut. 2000, 47:112-9.), stimulates intestinal hexose transport via the upregulation of glucose transporters (Cheeseman, Am J Physiol. 1997, R1965-71), and increases intestinal blood flow (Guan et al. Gastroenterology. 2003, 125, 136-47).

The beneficial effects of GLP-2 in the small intestine have raised considerable interest as to the use of GLP-2 in the treatment of intestinal disease or injury (Sinclair and Drucker, Physiology 2005: 357-65). Furthermore, GLP-2 has been shown to prevent or reduce mucosal epithelial damage in a wide number of preclinical models of gut injury, including chemotherapy-induced enteritis, ischemia-reperfusion injury, dextran sulfate-induced colitis and genetic models of inflammatory bowel disease (Sinclair and Drucker Physiology 2005: 357-65). The GLP-2 analogue teduglutide (Gly2-hGLP-2) is approved for treatment of short bowel syndrome under the trade names Gattex and Revestive.

GLP-1 is a peptide hormone known for its important role in glucose homeostasis. When secreted from the gastrointestinal tract in response to nutrient ingestion, GLP-1 potentiates glucose-stimulated insulin secretion from the β-cells (Kim and Egan, 2008, Pharmacol. Rev. 470-512). Furthermore, GLP-1 or it analogues has been shown to increase somatostatin secretion and suppress glucagon secretion (Hoist J J, 2007, Physiol Rev. 1409-1439).

Besides the primary actions of GLP-1 on glucose-stimulated insulin secretion, GLP-1 is also known as a key regulator of appetite, food intake, and body weight. Moreover, GLP-1 can inhibit gastric emptying and gastrointestinal motility in both rodents and humans, most likely through GLP-1 receptors present in the gastrointestinal tract (Hoist J J, 2007, Physio) Rev. 1409-1439; Hellström et al., 2008, Neurogastroenterol Motil. June; 20(6):649-659). In addition, GLP-1 seems to have insulin-like effects in major extrapancreatic tissues, participating in glucose homeostasis and lipid metabolism in tissues such as muscle, liver, and adipose tissues (Kim and Egan, 2008, Pharmacol. Rev. 470-512).

Thus the dual agonist compounds of the present invention may be used to increase intestinal mass, improve intestinal function (especially intestinal barrier function), increase intestinal blood flow, or repair intestinal damage or dysfunction (whether structural or functional), e.g. damage to the intestinal epithelium. They may also be used in the prophylaxis or treatment of conditions which may be ameliorated by these effects, and in reducing the morbidity related to gastrointestinal damage.

The dual agonists therefore find use in many gastrointestinal disorders. The term "gastrointestinal" is used here to include the entire gastrointestinal tract, including oesophagus, stomach, small intestine (duodenum, jejunum, ileum) and large intestine (cecum, colon, rectum), but especially the small intestine and colon.

Thus, conditions in which the dual agonists may be of benefit include malabsorption, ulcers (which may be of any aetiology, e.g., peptic ulcers, Zollinger-Ellison Syndrome, drug-induced ulcers, and ulcers related to infections or other pathogens), short-bowel syndrome, cul-de-sac syndrome, inflammatory bowel disease (Crohn's disease and ulcerative colitis), irritable bowel syndrome, pouchitis, celiac sprue (for example arising from gluten induced enteropathy or celiac disease), tropical sprue, hypogammaglobulinemic sprue and mucositis or diarrhea induced by chemotherapy or radiation therapy.

The dual agonists may also find use in certain conditions which do not primarily affect gastrointestinal tissue but which may be caused or exacerbated by factors arising from intestinal dysfunction. For example, impaired intestinal barrier function (which may be referred to as "leakiness" of the intestine or gut) can lead to transit of materials from the lumen of the gut directly into the bloodstream and thus to the kidney, lung and/or liver. These materials may include food molecules such as fats, which contribute to hepatitis and/or fatty liver diseases, including parenteral nutrition associated gut atrophy, PNALD (Parenteral Nutrition-Associated Liver Disease), NAFLD (Non-Alcoholic Fatty Liver Disease) and NASH (Non-Alcoholic Steatohepatitis). The materials crossing into the bloodstream may also include pathogens such as bacteria, and toxins such as bacterial lipopolysaccharide (LPS), which may contribute to systemic inflammation (e.g. vascular inflammation). Such inflammation is often referred to as "low grade inflammation" and is a contributing factor to the pathogenesis of metabolic endotoxemia (a condition seen in both diabetes and obesity, discussed further below), primary biliary cirrhosis and hepatitis. Entry of pathogens to the bloodstream may also result in conditions such as necrotising enterocolitis.

Low grade inflammation is not characterised by the normal symptoms of acute inflammation such as pain, fever and redness, but can be detected via the presence of inflammatory markers in the blood, such as C-reactive protein and pro-inflammatory cytokines including TNF-alpha (tumour necrosis factor alpha).

The dual agonists may also find use in conditions which primarily affect other tissues but have gastrointestinal side-effects. For example, inflammatory conditions such as pancreatitis result in elevated levels of circulating inflammatory mediators which may in turn induce intestinal damage or intestinal dysfunction, such as impairment of barrier function. In some circumstances, this may lead to more severe systemic inflammatory conditions such as sepsis, or to surgical procedures or mechanical injuries (volvulus) where blood supply to the intestine is interrupted, ultimately leading to ischaemia-reperfusion injuries.

Similarly, graft versus host disease (GVHD) may result in substantial tissue damage to the gastrointestinal tract, resulting in impaired barrier function and other side effects such as diarrhea. Thus, the dual agonists described may be useful for the prophylaxis or treatment of intestinal dysfunction or damage caused by or associated with GVHD, as well as prophylaxis or treatment of side effects such as diarrhea caused by or associated with GVHD.

The dual agonist compounds described herein also find use, inter alia, in reducing or inhibiting weight gain, reducing rate of gastric emptying or intestinal transit, reducing food intake, reducing appetite, or promoting weight loss. The effect on body weight may be mediated in part or wholly via reducing food intake, appetite or intestinal transit.

Thus the dual agonists of the invention can be used for the prophylaxis or treatment of obesity, morbid obesity, obesity-linked gallbladder disease and obesity-induced sleep apnea.

Independently of their effect on body weight, the dual agonists of the invention may have a beneficial effect on glucose tolerance and/or glucose control. They may also be used to modulate (e.g. improve) circulating cholesterol levels, being capable of lowering circulating triglyceride or LDL levels, and increasing HDL/LDL ratio.

Thus, they may be used for the prophylaxis or treatment of inadequate glucose control, glucose tolerance or dyslipidaemia (e.g. elevated LDL levels or reduced HDL/LDL ratio) and associated conditions, including diabetes (e.g. Type 2 diabetes, gestational diabetes), pre-diabetes, metabolic syndrome and hypertension.

Many of these conditions are also associated with obesity or overweight. The effects of the dual agonists on these conditions may therefore follow from their effect on body weight, in whole or in part, or may be independent thereof.

Effects on body weight may be therapeutic or cosmetic.

The dual agonist activity of the compounds described herein may be particularly beneficial in many of the conditions described, as the two activities may complement one another.

For example, malabsorption is a condition arising from abnormality in the absorption of water and/or food nutrients, such as amino acids, sugars, fats, vitamins or minerals, via the gastrointestinal (GI) tract, leading to malnutrition and/or dehydration. Malabsorption may be a result of physical (e.g. traumatic) or chemical damage to the intestinal tract. Dual agonists as described in this specification may be capable of improving intestinal barrier function, reducing gastric emptying, and increasing intestinal absorption while at the same time normalising intestinal transit time. This would not only help patients to increase the absorption of nutrients and liquid, but would also alleviate patients' social problems related to meal-stimulated bowel movements.

Furthermore, intestinal function and metabolic disorders may be closely inter-related, with each contributing to the development or symptoms of the other.

As mentioned above, obesity is linked with low grade inflammation (sometimes designated "obesity-linked inflammation"). It is also generally recognised that obesity (along with other syndromes) causes an increased vascular permeability which allows pathogens and toxins such as LPS to enter the cell wall of the intestinal tract and thereby initiate inflammation. The changes that result from the inflammatory response are essentially the same regardless of the cause and regardless of where the insult arises. The inflammatory response may be acute (short lived) or chronic (longer lasting).

It has been demonstrated that, e.g., obese mice (ob/ob and db/db mice) have a disrupted mucosal barrier function and exhibit increased low-grade inflammation (Brun et al., 2007, Am. J. Physiol. Gastrointest. Liver Physiol., 292: G518-G525, Epub 5 Oct. 2006). These observations were further extended to C57BL6/J mice maintained on a high-fat diet (Cani et al., 2008, Diabetes, vol. 57, 1470-1481) and to non-obese diabetic mice (Hadjiyanni et al., 2009, Endocrinology, 150(2): 592-599).

Cani and colleagues (Gut; 2009, 58:1091-1103,) reported that in ob/ob mice, the modulation of the gut microbiota resulted in decreased intestinal barrier dysfunction and reduced systemic inflammation via a GLP-2 dependent pathway. Further, the increased intestinal permeability observed in obese and diabetic patients is likely to play a more vital role in the disease progression than previously anticipated. Increased intestinal permeability leads to increased bacterial lipopolysaccharide (LPS) transport across the intestinal barrier. This increased LPS activates immune cells, such as circulating macrophages and macrophages residing in organs in the body, causing low-grade chronic inflammation that may be involved in the pathogenesis of many diseases. This phenomenon is called metabolic endotoxemia (ME).

The inflammatory process may also play a role in causing metabolic dysfunction in obese individuals, such as insulin resistance and other metabolic disturbances.

Thus the dual agonist compounds of the invention may be particularly useful for prophylaxis or treatment of low grade inflammation, especially in obese or overweight individuals, exerting beneficial effects via the GLP-1 agonist component of their activity and/or the GLP-2 component of their activity.

The therapeutic efficacy of treatment with a dual agonist of the invention may be monitored by enteric biopsy to examine the villus morphology, by biochemical assessment of nutrient absorption, by non-invasive determination of intestinal permeability, by patient weight gain, or by amelioration of the symptoms associated with these conditions.

In a further aspect there is provided a therapeutic kit comprising a dual agonist of the invention, or a pharmaceutically acceptable salt or solvate thereof.

The following examples are provided to illustrate preferred aspects of the invention and are not intended to limit the scope of the invention in any way.

EXAMPLES

The following examples are provided to illustrate preferred aspects of the invention and are not intended to limit the scope of the invention.

Materials and Methods

General Peptide Synthesis

List of abbreviations and suppliers are provided in the table below

| List of abbreviations and suppliers | | |
|---|---|---|
| Abbreviation | Name | Brand/Supplyer |
| Resins | TentaGel ™ PHB AA(Proct)-Fmoc | Rapp Polymere |
| | TentaGel ™ SRAM | Rapp Polymere |
| Amino acids | Pseudoprolines (E.g. QT, AT, FS) | Jupiter Bioscience Ltd. |
| | Fmoc-L-AA-OH | Senn Chemicals AG |

-continued

List of abbreviations and suppliers

| | Abbreviation | Name | Brand/Supplyer |
|---|---|---|---|
| Coupling reagents | COMU | (1-Cyano-2-ethoxy-2-oxoethylidenaminooxy)dimethylamino-morpholino-carbenium hexafluorophosphate | Watson International Ltd. |
| | DIC | Diisopropylcarbodiimide | Fluka/Sigma Aldrich Co. |
| | HATU | N-[(dimethylamino)-1H-1,2,3-triazol[4,5-b]pyridine-1-ylmethylene]-N-methylmethanaminium hexafluorophosphate N-oxide | ChemPeP Inc. |
| | HOBt | Hydroxybenzotriazole | Sigma-Aldrich Co. |
| Solvents reagents | $Boc_2O$ | Di-tert-butyl pyrocarbonate | Advanced ChemTech |
| | DCM | Dichloromethane | Prolabo (VWR) |
| | DIPEA | Diisopropylethylamine | Fluka/Sigma Aldrich Co. |
| | DMF | N,N-dimethylformamide | Taminco |
| | DODT | 3,6-dioxa-1,8-octanedithiol | Sigma-Aldrich Co. |
| | $Et_2O$ | Diethyl ether | Prolabo (VWR) |
| | EtOH | Ethanol | CCS Healthcare AB |
| | | Formic acid (HPLC) | Sigma-Aldrich Co. |
| | $H_2O$ | Water, Milli-Q water | Millipore |
| | MeCN | Acetonitrile (HPLC) | Sigma-Aldrich Co. |
| | NMP | N-methylpyrrolidone | Sigma-Aldrich Co. |
| | | Piperidine | Jubliant Life Sciences Ltd. |
| | TFA | Trifluoroacetic acid (HPLC) | Chemicals Raw Materials Ltd. |
| | TIS | Triisopropylsilane | Sigma-Aldrich Co. |
| | MeOH | Methanol | Sigma-Aldrich Co. |

Apparatus and Synthetic Strategy

Peptides were synthesized batchwise on a peptide synthezier, such as a CEM Liberty Peptide Synthesizer or a Symphony X Synthesizer, according to solid phase peptide synthetic procedures using 9-fluorenylmethyloxycarbonyl (Fmoc) as N-α-amino protecting group and suitable common protection groups for side-chain functionalities.

As polymeric support based resins, such as e.g. TentaGel™, was used. The synthesizer was loaded with resin that prior to usage was swelled in DMF.

Coupling

CEM Liberty Peptide Synthesizer

A solution of Fmoc-protected amino acid (4 equiv.) was added to the resin together with a coupling reagent solution (4 equiv.) and a solution of base (8 equiv.). The mixture was either heated by the microwave unit to 70-75° C. and coupled for 5 minutes or coupled with no heat for 60 minutes. During the coupling nitrogen was bubbled through the mixture.

Symphony X Synthesizer

The coupling solutions were transferred to the reaction vessels in the following order: amino acid (4 equiv.), HATU (4 equiv.) and DIPEA (8 equiv.). The coupling time was 10 min at room temperature (RT) unless otherwise stated. The resin was washed with DMF (5×0.5 min). In case of repeated couplings the coupling time was in all cases 45 min at RT.

Deprotection

CEM Liberty Peptide Synthesizer

The Fmoc group was deprotected using piperidine in DMF or other suitable solvents. The deprotection solution was added to the reaction vessel and the mixture was heated for 30 sec. reaching approx. 40° C. The reaction vessel was drained and fresh deprotection solution was added and subsequently heated to 70-75° C. for 3 min. After draining the reaction vessel the resin was washed with DMF or other suitable solvents.

Symphony X Synthesizer

Fmoc deprotection was performed for 2.5 minutes using 40% piperidine in DMF and repeated using the same conditions. The resin was washed with DMF (5×0.5 min).

Cleavage

The dried peptide resin was treated with TFA and suitable scavengers for approximately 2 hours. The volume of the filtrate was reduced and the crude peptide was precipitated after addition of diethylether. The crude peptide precipitate was washed several times with diethylether and finally dried.

HPLC Purification of the Crude Peptide

The crude peptide was purified by preparative reverse phase HPLC using a conventional HPLC apparatus, such as a Gilson GX-281 with 331/332 pump combination', for binary gradient application equipped with a column, such as 5×25 cm Gemini NX 5u C18 110A column, and a fraction collector using a flow 20-40 ml/min with a suitable gradient of buffer A (0.1% Fomic acid, aq.) or A (0.1% TFA, aq.) and buffer B (0.1% Formic acid, 90% MeCN, aq.) or B (0.1% TFA, 90% MeCN, aq.). Fractions were analyzed by analytical HPLC and MS and selected fractions were pooled and lyophilized. The final product was characterized by HPLC and MS.

Analytical HPLC

Final purities were determined by analytic HPLC (Agilent 1100/1200 series) equipped with auto sampler, degasser, 20 µl flow cell and Chromeleon software. The HPLC was operated with a flow of 1.2 ml/min at 40° C. using an analytical column, such as Kinetex 2.6 µm XB-C18 100A 100×4.6 mm column. The compound was detected and quantified at 215 nm. Buffers A (0.1% TFA, aq.) and buffer B (0.1% TFA, 90% MeCN, aq.).

Mass Spectroscopy

Final MS analysis were determined on a conventional mass spectroscopy, e.g. Waters Xevo G2 Tof, equipped with electrospray detector with lock-mass calibration and MassLynx software. It was operated in positive mode using direct injection and a cone voltage of 15V (1 TOF), 30 V (2 TOF) or 45 V (3 TOF) as specified on the chromatogram. Precision was 5 ppm with a typical resolution of 15,000-20,000.

GLP-1 and GLP-2 Receptor Efficacy Assays

Peptides of this invention function as both GLP-1 and GLP-2 agonists and thus activate the GLP-1 receptor and GLP-2 receptor, respectively. One useful in vitro assay for measuring GLP-1 and GLP-2 receptor activity is quantitation of cAMP, i.e. 3'-5'-cyclic adenosine monophosphate, which is a second messenger essential in many biological processes, and one of the most ubiquitous mechanisms for regulating cellular functions. An example is the cAMP AlphaScreen® assay from Perkin Elmer which has been used to quantitate the cAMP response upon GLP-1 and GLP-2 receptor activation in HEK293 cells stably expressing GLP-1R or GLP-2R. Test compounds eliciting an increase in the intracellular level of cAMP can be tested in these assays, and the response normalized relative to a positive and negative control (vehicle) to calculate the EC50 and maximal response from the concentration response curve using the 4-parameter logistic (4PL) nonlinear model for curve fitting.

Example 1: Synthesis of the Compounds

Compounds Synthesised

The following compounds of Table 1 were synthesized using the above techniques.

TABLE 1.1

| | Compounds synthesized |
|---|---|
| 1 | Hy-H[Aib]EGSFTSELATILDEQAARDFIAWLIAHKITD-OH (SEQ ID NO: 6) |
| 2 | Hy-H[Aib]EGTFSSELATILDEQAARDFIAWLIAHKITD-OH (SEQ ID NO: 7) |
| 3 | Hy-H[Aib]EGTFTSELATILDEQAARDFIAWLIAHKITD-OH (SEQ ID NO: 8) |
| 4 | Hy-H[Aib]EGSFTSELATILDEQAARDFIAWLIEHKITD-OH (SEQ ID NO: 9) |
| 5 | Hy-H[Aib]EGTFTSELATILDEQAARDFIAWLIEHKITD-OH (SEQ ID NO: 10) |
| 6 | Hy-H[Aib]EGSFTSELATILDEQAARDFIAWLIHHKITD-OH (SEQ ID NO: 11) |
| 7 | Hy-H[Aib]EGSFTSELATILDEQAARDFIAWLIYHKITD-OH (SEQ ID NO: 12) |
| 8 | Hy-H[Aib]EGSFTSELATILDEQAARDFIAWLILHKITD-OH (SEQ ID NO: 13) |
| 9 | Hy-H[Aib]EGTFTDELATILDEQAARDFIAWLIAHKITD-OH (SEQ ID NO: 14) |
| 10 | Hy-H[Aib]EGTFTSELSTILDEQAARDFIAWLIAHKITD-OH (SEQ ID NO: 15) |
| 11 | Hy-H[Aib]EGTFTSELATILDGKAARDFIAWLIAHKITD-OH (SEQ ID NO: 16) |
| 12 | Hy-H[Aib]EGTFTSELATILDEQAARDFIAWLHAHKITD-OH (SEQ ID NO: 17) |
| 13 | Hy-H[Aib]EGTFTSELATILDEQAARDFIAWLQAHKITD-OH (SEQ ID NO: 18) |

TABLE 1.1-continued

| | Compounds synthesized |
|---|---|
| 14 | Hy-H[Aib]EGTFTSELATILDEQAARDFIAWLYAHKITD-OH (SEQ ID NO: 19) |
| 15 | Hy-H[Aib]EGTFTSELATILDEQAARDFIAWLIQHKITD-OH (SEQ ID NO: 20) |
| 16 | Hy-H[Aib]EGTFTSELATILDEQAARDFIAWLIKHKITD-OH (SEQ ID NO: 21) |
| 17 | Hy-H[Aib]EGTFTSELATILDEQAARDFIAWLIRHKITD-OH (SEQ ID NO: 22) |
| 18 | Hy-H[Aib]EGTFTSELATILDEQAARDFIAWLISHKITD-OH (SEQ ID NO: 23) |
| 19 | Hy-H[Aib]EGTFTSELATILDEQAARDFIAWLIAQKITD-OH (SEQ ID NO: 24) |
| 20 | Hy-H[Aib]EGTFTSELATILDEQAARDFIAWLIAYKITD-OH (SEQ ID NO: 25) |
| 21 | Hy-H[Aib]EGTFTSELATILDEQAARDFIAWLHQHKITD-OH (SEQ ID NO: 26) |
| 22 | Hy-H[Aib]EGSFTSELATILDEQAARDFIAWLHAHKITD-OH (SEQ ID NO: 27) |
| 23 | Hy-H[Aib]EGSFTSELATILDEQAARDFIAWLYEHKITD-OH (SEQ ID NO: 28) |
| 24 | Hy-H[Aib]EGSFTSELATILDEQAARDFIAWLQAHKITD-OH (SEQ ID NO: 29) |
| 25 | Hy-H[Aib]EGSFTSELATILDEQAARDFIAWLIAQKITD-OH (SEQ ID NO: 30) |
| 26 | Hy-H[Aib]EGTFTSELATILDEQAARDFIAWLQAQKITD-OH (SEQ ID NO: 31) |
| 27 | Hy-H[Aib]EGTFTSELATILDEQAARDFIAWLQAQKITD-OH (SEQ ID NO: 32) |
| 28 | Hy-H[Aib]EGSFTSELATILDEQAARDFIAWLYAHKITD-OH (SEQ ID NO: 33) |
| 29 | Hy-H[Aib]EGTFTSELSTILDEQAARDFIAWLQAQKITD-OH (SEQ ID NO: 34) |
| 30 | Hy-H[Aib]EGSFTSELATILDEQAARDFIAWLHAQKITD-OH (SEQ ID NO: 35) |
| 31 | Hy-H[Aib]EGSFTSELATILDGKAARDFIAWLIAHKITD-OH (SEQ ID NO: 36) |
| 32 | Hy-H[Aib]EGTFSSELATILDGKAARDFIAWLIAHKITD-OH (SEQ ID NO: 37) |
| 33 | Hy-H[Aib]EGTFTSELATILDEQAARDFINWLIAHKITD-OH (SEQ ID NO: 38) |
| 34 | Hy-H[Aib]EGTFTSELATILDEQAARDFISWLIAHKITD-OH (SEQ ID NO: 39) |
| 35 | Hy-H[Aib]EGTFTSELATILDEQAARDFINWLKAHKITD-OH (SEQ ID NO: 40) |
| 36 | Hy-H[Aib]EGTFTSELATILDEQAARDFINWLKSYKITD-OH (SEQ ID NO: 41) |
| 37 | Hy-H[Aib]EGTFTSELATILDEQAARDFINWLKEQKITD-OH (SEQ ID NO: 42) |
| 38 | Hy-HGEGTFTSELATILDEQAARDFIAWLIAHKITD-OH (SEQ ID NO: 43) |
| 39 | Hy-H[Aib]EGTFSSELSTILEEQASREFIAWLIAHKITE-OH (SEQ ID NO: 44) |

TABLE 1.1-continued

Compounds synthesized

| | | |
|---|---|---|
| 40 | Hy-HGEGSFSSELATILDEQAARDFIAWLIQHKITD-[NH2] | (SEQ ID NO: 45) |
| 41 | Hy-H[Aib]EGSFSSELATILDEQAARDFIAWLIQHKITD-OH | (SEQ ID NO: 46) |

For illustration purposes only, the synthesis of two selected compounds is described in detail below.

Synthesis of Compound 2

Hy-H[Aib]EGTFSSELATILDEQAARDFIAWLIAHKITD-OH (SEQ ID NO: 7)

Solid phase peptide synthesis was performed on a Symphony X Synthesizer using standard Fmoc chemistry. TentaGel S PHB Asp(tBu)Fmoc (1.22 g; 0.23 mmol/g) was swelled in DMF (10 ml) prior to use and the Fmoc-group was deprotected according to the procedure described above.

Coupling

Suitable protected Fmoc-amino acids according to the sequence were coupled as described above using HATU as coupling reagent. All couplings were performed at R.T. In order to facilitate the synthesis, a pseudoproline were used: in position 6 and 7 Fmoc-Phe-Ser(psi Me,Mepro)-OH. The pseudoproline was coupled according to the standard procedure described above for Fmoc-amino acids.

Deprotection

Fmoc deprotection was performed according to the procedure described above.

Cleavage of the Peptide from the Solid Support

The peptide-resin was washed with EtOH (3×10 ml) and Et2O (3×10 ml) and dried to constant weight at room temperature (r.t.). The peptide was cleaved from the resin by treatment with TFA/TIS/$H_2O$ (95/2.5/2.5; 40 ml, 2 h; r.t.). The volume of the filtrate was reduced and the crude peptide was precipitated after addition of diethylether. The crude peptide precipitate was washed several times with diethylether and finally dried to constant weight at room temperature yield 950 mg crude peptide product (purity ~48%).

HPLC Purification of the Crude Peptide

The crude peptide was purified by preparative reverse phase HPLC using a Gilson GX-281 with 331/332 pump combination for binary gradient application equipped with a 5×25 cm Gemini NX 5u C18 110A, column and a fraction collector and run at 30 ml/min with a gradient of buffer A (0.1% TFA, aq.) and buffer B (0.1% TFA, 90% MeCN, aq.) gradient from 30% B to 60% B in 47 min. Fractions were analyzed by analytical HPLC and MS and relevant fractions were pooled and lyophilized to yield 224 mg, with a purity of 93% as characterized by HPLC and MS as described above. Calculated monoisotopic MW=3682.86, found 3682.87.

Synthesis of Compound 7

Hy-H[Aib]EGSFTSELATILDEQAARDFIAWLIYHKITD-OH (SEQ ID NO: 12)

Solid phase peptide synthesis was performed on a Symphony X Synthesizer using standard Fmoc chemistry. TentaGel S PHB Asp(tBu)Fmoc (1.19 g; 0.23 mmol/g) was swelled in DMF (10 ml) prior to use and the Fmoc-group was deprotected according to the procedure described above.

Coupling

Suitable protected Fmoc-amino acids according to the sequence were coupled as described above using HATU as coupling reagent. All couplings were performed at R.T. In order to facilitate the synthesis, a pseudoproline were used: in position 6 and 7 Fmoc-Phe-Thr(psi Me,Mepro)-OH. The pseudoproline was coupled according to the standard procedure described above for Fmoc-amino acids.

Deprotection

Fmoc deprotection was performed according to the procedure described above.

Cleavage of the Peptide from the Solid Support

The peptide-resin was washed with EtOH (3×10 ml) and Et2O (3×10 ml) and dried to constant weight at room temperature (r.t.). The peptide was cleaved from the resin by treatment with TFA/TIS/$H_2O$ (95/2.5/2.5; 40 ml, 2 h; r.t.). The volume of the filtrate was reduced and the crude peptide was precipitated after addition of diethylether. The crude peptide precipitate was washed several times with diethylether and finally dried to constant weight at room temperature yield 750 mg crude peptide product (purity ~30%).

HPLC Purification of the Crude Peptide

The crude peptide was purified by preparative reverse phase HPLC using a Gilson GX-281 with 331/332 pump combination for binary gradient application equipped with a 5×25 cm Gemini NX 5u C18 110A, column and a fraction collector and run at 30 ml/min with a gradient of buffer A (0.1% TFA, aq.) and buffer B (0.1% TFA, 90% MeCN, aq.) gradient from 30% B to 60% B in 47 min. Fractions were analyzed by analytical HPLC and MS and relevant fractions were pooled and lyophilized to yield 53 mg, with a purity of 84% as characterized by HPLC and MS as described above. Calculated monoisotopic MW=3774.89, found 3774.87.

Example 2: GLP-1R and GLP-2R $EC_{50}$ Measurements

Generation of Cell Line Expressing Human GLP-1 Receptors

The cDNA encoding the human glucagon-like peptide 1 receptor (GLP-1R) (primary accession number P43220) was cloned from the cDNA BC112126 (MGC:138331/IMAGE: 8327594). The DNA encoding the GLP-1-R was amplified by PCR using primers encoding terminal restriction sites for subcloning. The 5'-end primers additionally encoded a near Kozak consensus sequence to ensure efficient translation. The fidelity of the DNA encoding the GLP-1-R was confirmed by DNA sequencing. The PCR products encoding the GLP-1-R were subcloned into a mammalian expression vector containing a neomycin (G418) resistance marker. The mammalian expression vectors encoding the GLP-1-R were transfected into HEK293 cells by a standard calcium phosphate transfection method. 48 hours post-transfection, cells were seeded for limited dilution cloning and selected with 1 mg/ml G418 in the culture medium. Following 3 weeks in G418 selection clones were picked and tested in a functional GLP-1 receptor potency assay as described below. One clone was selected for use in compound profiling.

Generation of Cell Line Expressing Human GLP-2 Receptors

The hGLP2-R was purchased from MRC-geneservice, Babraham, Cambridge as an Image clone: 5363415 (11924-I17). For subcloning into a mammalian expression vector, primers for subcloning were obtained from DNA-Technology, Risskov, Denmark. The 5' and 3' primers used for the PCR reaction include terminal restriction sites for cloning and the context of the 5' primer is modified to a Kozak consensus without changing the sequence of the product encoded by the ORF. A standard PCR reaction was run using Image clone 5363415 (11924-117) as a template with the above mentioned primers and Polymerase Herculase II Fusion in a total vol. of 50 µl. The generated PCR product was purified using GFX PCR and Gel band purification kit, digested with restriction enzymes and cloned into the mammalian expression vector using Rapid DNA Ligation Kit. Ligation reaction was transformed to XL10 Gold Ultracompetent cells and colonies were picked for DNA production using Endofree Plasmid maxi kit. Subsequent sequence analysis was conducted by MWG Eurofins, Germany. The clone was confirmed to be the hGLP-2 (1-33) receptor, splice variant rs17681684.

HEK293 cells were transfected using the Lipofectamine PLUS transfection method. The day before transfection, HEK293 cells were seeded in two T75 flasks at a density of $2 \times 10^6$ cells/T75 flask in cell culturing medium without antibiotics. On the day of transfection, cells were washed with 1×DPBS and medium was replaced with Optimem to a volume of 5 mL/T75 flask before addition of Lipofectamine-plasmid complexes were added gently and drop wise to the cells in T75 flasks and replaced with growth medium after 3 hours and again to growth medium supplemented with 500 µg/mL G418 after 24 hours. Following 4 weeks in G418 selection, clones were picked and tested in a functional GLP-2 receptor potency assay as described below. One clone was selected for use in compound profiling.

GLP-1R and GLP-2 Receptor Potency Assays

The cAMP AlphaScreen assay from Perkin Elmer was used to quantitate the cAMP response to activation of the GLP1 and GLP2 receptor, respectively. Exendin-4 was used as reference compound for GLP1 receptor activation and Teduglutide as reference compound for GLP2 receptor activation. Data from test compounds eliciting an increase in the intracellular level of cAMP were normalized relative to the positive and negative control (vehicle) to calculate the $EC_{50}$ and maximal response from the concentration response curve. The results are listed in Table 2.

TABLE 2

| Compound | $EC_{50}$ GLP-1 (nM) | $EC_{50}$ GLP-2 (nM) |
|---|---|---|
| Teduglutide | 39.0 | 0.027 |
| Liraglutide | 0.029 | N/A |
| 1 | 0.014 | 0.036 |
| 2 | 0.046 | 0.034 |
| 3 | 0.0074 | 0.036 |
| 4 | 0.015 | 0.044 |
| 5 | 0.0098 | 0.067 |
| 6 | 0.014 | 0.047 |
| 7 | 0.017 | 0.110 |

TABLE 2-continued

| Compound | $EC_{50}$ GLP-1 (nM) | $EC_{50}$ GLP-2 (nM) |
|---|---|---|
| 8 | 0.021 | 0.084 |
| 9 | 0.007 | 0.041 |
| 10 | 0.005 | 0.050 |
| 11 | 0.011 | 0.085 |
| 12 | 0.055 | 0.076 |
| 13 | 0.016 | 0.083 |
| 14 | 0.021 | 0.049 |
| 15 | 0.005 | 0.038 |
| 16 | 0.006 | 0.026 |
| 17 | 0.006 | 0.066 |
| 18 | 0.006 | 0.054 |
| 19 | 0.005 | 0.150 |
| 20 | 0.012 | 0.260 |
| 21 | 0.049 | 0.110 |
| 22 | 0.280 | 0.042 |
| 23 | 0.120 | 0.034 |
| 24 | 0.042 | 0.049 |
| 25 | 0.008 | 0.062 |
| 26 | 0.013 | 0.190 |
| 27 | 0.120 | 0.370 |
| 28 | 0.110 | 0.024 |
| 29 | 0.044 | 0.110 |
| 30 | 0.100 | 0.034 |
| 31 | 0.020 | 0.078 |
| 32 | 0.038 | 0.150 |
| 33 | 0.004 | 0.041 |
| 34 | 0.005 | 0.049 |
| 35 | 0.006 | 0.048 |
| 36 | 0.007 | 0.110 |
| 37 | 0.007 | 0.160 |
| 38 | 0.008 | 0.043 |
| 39 | 0.030 | 0.960 |
| 40 | 1.400 | 0.050 |
| 41 | 0.078 | 0.026 |

N/A = no detectable activity

Example 3: Solubility Assessment

A stock solution of the test peptide (2 mg/ml; determined from the weighed amount of peptide) in demineralized water adjusted to pH 2.5 with HCl was prepared, and aliquots were diluted 1:1 in 100 mM acetate buffer (pH 4.0 and pH 5.0), 100 mM histidine buffer (pH 6.0 and pH 7.0) and 100 mM phosphate buffer (pH 6.0, pH 7.0 and pH7.5), respectively, and loaded in a standard flat-bottom, non-sterile 96-well UV Microplate. The absorbance of samples (single samples, n=1) at 280 and 325 nm was measured in an absorbance-based plate reader, which was preheated to ambient temperature (typically 25° C.). The turbidity absorbance criterion for a peptide solubility of ≥1 mg/ml was an absorbance at 325 nm of ≤0.025 absorbance units (which is 5 to 6 times the standard deviation of 8 buffer samples in a plate). Solubility data for peptides of the invention are shown in Table 3, below.

TABLE 3

| | Solubility data | | | | | | |
|---|---|---|---|---|---|---|---|
| Cpd | Acetate buffer pH 4 | Acetate buffer pH 5 | Histidine buffer pH 6 | Histidine buffer pH 7 | Phosphate buffer pH 6 | Phosphate buffer pH 7 | Phosphate buffer pH 7.5 |
| 1 | SS | II | SS | SS | SS | SS | SS |
| 3 | SS | II | SS | SS | SS | SS | SS |
| 4 | SS | II | SS | SS | SS | SS | SS |
| 5 | SS | II | SS | SS | SS | SS | SS |
| 6 | SS | II | II | SS | II | SS | II |

TABLE 3-continued

Solubility data.

| Cpd | Acetate buffer pH 4 | Acetate buffer pH 5 | Histidine buffer pH 6 | Histidine buffer pH 7 | Phosphate buffer pH 6 | Phosphate buffer pH 7 | Phosphate buffer pH 7.5 |
|---|---|---|---|---|---|---|---|
| 7 | SS | II | II | SS | II | SS | SS |
| 8 | SS | II | II | SS | II | SS | SS |

*SS indicates solubility ≥1 mg/ml
**II indicates solubility <1 mg/ml

Example 4: Chemical Stability

Samples of each test peptide were dissolved in MilliQ™ water, and the pH of the solution was adjusted to pH 6, 7, 7.5 or 9 using either HCl or NaOH. The final peptide concentration was 0.2 mg/ml. Samples were placed in glass vials and incubated at 40° C. The samples were analyzed by RP-HPLC on a C18 column with gradient elution using an acetonitrile/TFA/water eluent system. The area-percentage (area-%) of the main peak after incubation time T=t (relative to time T=0) was determined by UV spectroscopy at 220 nm.

The purity was first determined as follows:

Purity (area-%)=(area of main peak/total area of all peaks)×100.

The purity was then normalized between time points by setting purity at time 0 (T=0) to 100 for each pH value for a given peptide, as follows:

Normalised area-% at time $t$ ($T=t$)=[area-% ($T=t$)/area-% ($T=0$)]×100.

The chemical stability assessment results after 14 day incubation (in the form of normalized purity values) are summarized in Table 4.

TABLE 4

Chemical stability data.

| Compound | pH 6 normalised stability | pH 7 normalised stability |
|---|---|---|
| 1 | A | B |
| 3 | A | B |
| 5 | A | B |
| 4 | C | A |
| 6 | C | C |
| 7 | C | C |
| 8 | C | C |
| 26 | C | B |
| 29 | C | B |
| 34 | C | C |
| 35 | C | C |
| 10 | NA | C |
| 31 | NA | C |
| 38 | NA | C |
| 41 | C | A |

TABLE 4-continued

Chemical stability data.

| Compound | pH 6 normalised stability | pH 7 normalised stability |
|---|---|---|
| 2 | C | A |
| 22 | NA | C |

Key:
A—>90% normalised stability;
B—>80% stability;
C—<80% normalized stability.

Example 5: Effect on Fasting Glucose and Intestinal Weight in Normal Mice

Normal chow-fed C57BL/6J male mice were used. The mice were kept in standard housing conditions, light-, temperature-, and humidity-controlled room (12:12 h light-dark cycle, with lights on at 06.00-18.00 h; 20-22° C.; 50-80% relative humidity). Each dosing group consisted of 6 animals. Mice were dosed once daily with 250 nmol/kg with the test compounds or vehicle for 4 days via subcutaneous administration.

On day 0 mice were fasted and blood glucose levels measured after a single s.c. injection with peptides. Animals were sacrificed 24 hours after final dosing on day 3, and small intestinal wet weights were measured.

Results

All test compounds (250 nmol/kg) reduced fasting blood glucose levels compared to vehicle group (Table 5).

Test compounds increased small intestine wet weight as compared to the vehicle-treated mice (Table 5).

TABLE 5

Effects on fasting blood glucose levels and small intestinal weight.

| Treatment | Fasting blood glucose (mM) | Small intestinal wet weight (g) |
|---|---|---|
| Vehicle | 8.24 | 0.76 |
| Cpd. 1 | 5.76 | 0.90 |
| Cpd. 5 | 5.43 | 0.90 |
| Cpd. 22 | 6.18 | 0.82 |
| Cpd. 26 | 5.70 | 0.78 |
| Cpd. 34 | 5.62 | 0.93 |
| Cpd. 35 | 5.95 | 0.81 |

The invention claimed is:

1. A glucagon-like peptide 1 (GLP-1)/glucagon-like peptide 2 (GLP-2) dual agonist represented by the formula:

$$R^1-X^*-U-R^2,$$

wherein:
R¹ is hydrogen (Hy), C₁₋₄ alkyl, acetyl, formyl, benzoyl or trifluoroacetyl;
R² is NH₂ or OH;
X* is a peptide of formula I:

(I)
(SEQ ID NO: 3)
H-X2-EG-X5-F-X7-X8-E-X10-X11-TIL-X15-X16-X17-A-X19-X20-X21-FI-X24-WL-X27-X28-X29-KIT-X33, wherein:
X2 is Aib;
X5 is S or T;
X7 is S or T;
X8 is S or D;
X10 is L;
X11 is A or S;
X15 is D or E;
X16 is E or G;
X17 is Q or K;
X19 is A or S;
X20 is R;
X21 is D or E;
X24 is A, N or S;
X27 is I, Y, Q or K;
X28 is A, E, H, Y, or L;
X29 is H, Y or Q;
X33 is D;
U is absent or a sequence of 1-15 residues, each independently selected from K and k;
and wherein at least one of X5 and X7 is T;
or a pharmaceutically acceptable salt thereof.

2. The dual agonist or pharmaceutically acceptable salt thereof according to claim 1, wherein X8 is S, X7 is T, X5 is T, X29 is H and/or X27 is I.

3. The dual agonist or pharmaceutically acceptable salt thereof according to claim 1, wherein X27 is Q and X29 is Q.

4. The dual agonist or pharmaceutically acceptable salt thereof according to claim 1, wherein X11 is A, and/or, X16 is E and X17 is Q, and/or X16 is G and X17 is K.

5. The dual agonist or pharmaceutically acceptable salt thereof according to claim 1, wherein:
X11 is S and X15 is E;
X11 is S and X19 is S;
X11 is S and X21 is E;
X15 is E and X19 is S;
X15 is E and X21 is E;
X11 is S, X15 is E and X19 is S;
X11 is S, X15 is E and X21 is E;
X11 is S, X19 is S and X21 is E;
X15 is E, X19 is S and X21 is E; or
X11 is S, X15 is E, X19 is S and X21 is E.

6. The dual agonist or pharmaceutically acceptable salt thereof according claim 1, wherein residues X8-X24 contain a maximum of four changes compared to the sequence SELATILDEQAARDFIA (SEQ ID NO: 4).

7. The dual agonist or pharmaceutically acceptable salt thereof according to claim 1, wherein the residues at X27-X29 are selected from:

IAH;
QAH;
YAH;
IAQ;
IAY;
YEH;
QAQ;
KAH;
KEQ;
IEH; and
ILH.

8. The dual agonist or pharmaceutically acceptable salt thereof according to claim 1, wherein X* is a peptide of formula II:

(II)
(SEQ ID NO: 5)
H[Aib]EG-X5-F-X7-SELATILDEQAARDFIAWLI-X28-X29-KITD, wherein:
X5 is S or T;
X7 is S or T;
X28 is A, E, H, Y or L;
X29 is H, Y or Q;
and wherein at least one of X5 and X7 is T.

9. The dual agonist or pharmaceutically acceptable salt thereof according to claim 1, wherein U is a peptide sequence of 1-10 lysine residues.

10. The dual agonist or pharmaceutically acceptable salt thereof according to claim 1, wherein R¹ is Hy and/or R² is OH.

11. The dual agonist or pharmaceutically acceptable salt thereof according to claim 1, wherein X* consists of the sequence:

(SEQ ID NO: 6)
H[Aib]EGSFTSELATILDEQAARDFIAWLIAHKITD;

(SEQ ID NO: 7)
H[Aib]EGTFSSELATILDEQAARDFIAWLIAHKITD;

(SEQ ID NO: 8)
H[Aib]EGTFTSELATILDEQAARDFIAWLIAHKITD;

(SEQ ID NO: 9)
H[Aib]EGSFTSELATILDEQAARDFIAWLIEHKITD;

(SEQ ID NO: 10)
H[Aib]EGTFTSELATILDEQAARDFIAWLIEHKITD;

(SEQ ID NO: 11)
H[Aib]EGSFTSELATILDEQAARDFIAWLIHHKITD;

(SEQ ID NO: 12)
H[Aib]EGSFTSELATILDEQAARDFIAWLIYHKITD;

(SEQ ID NO: 13)
H[Aib]EGSFTSELATILDEQAARDFIAWLILHKITD;

(SEQ ID NO: 14)
H[Aib]EGTFTDELATILDEQAARDFIAWLIAHKITD;

(SEQ ID NO: 15)
H[Aib]EGTFTSELSTILDEQAARDFIAWLIAHKITD;

(SEQ ID NO: 16)
H[Aib]EGTFTSELATILDGKAARDFIAWLIAHKITD;

(SEQ ID NO: 18)
H[Aib]EGTFTSELATILDEQAARDFIAWLQAHKITD;

```
                                        (SEQ ID NO: 19)
H[Aib]EGTFTSELATILDEQAARDFIAWLYAHKITD;

(SEQ ID NO: 24)
H[Aib]EGTFTSELATILDEQAARDFIAWLIAQKITD;

(SEQ ID NO: 25)
H[Aib]EGTFTSELATILDEQAARDFIAWLIAYKITD;

(SEQ ID NO: 28)
H[Aib]EGSFTSELATILDEQAARDFIAWLYEHKITD;

(SEQ ID NO: 29)
H[Aib]EGSFTSELATILDEQAARDFIAWLQAHKITD;

(SEQ ID NO: 30)
H[Aib]EGSFTSELATILDEQAARDFIAWLIAQKITD;

(SEQ ID NO: 31)
H[Aib]EGTFTSELATILDEQAARDFIAWLQAQKITD;

(SEQ ID NO: 33)
H[Aib]EGSFTSELATILDEQAARDFIAWLYAHKITD;

(SEQ ID NO: 34)
H[Aib]EGTFTDELATILDEQAARDFIAWLQAQKITD;

(SEQ ID NO: 36)
H[Aib]EGSFTSELATILDGKAARDFIAWLIAHKITD;

(SEQ ID NO: 37)
H[Aib]EGTFSSELATILDGKAARDFIAWLIAHKITD;

(SEQ ID NO: 38)
H[Aib]EGTFTSELATILDEQAARDFINWLIAHKITD;

(SEQ ID NO: 39)
H[Aib]EGTFTSELATILDEQAARDFISWLIAHKITD;

(SEQ ID NO: 40)
H[Aib]EGTFTSELATILDEQAARDFINWLKAHKITD;
or (SEQ ID NO: 42)
H[Aib]EGTFTSELATILDEQAARDFINWLKEQKITD, (SEQ ID NO: 46)
H[Aib]EGSFSSELATILDEQAARDFIAWLIQHKITD.
```

12. The dual agonist or pharmaceutically acceptable salt thereof according to claim 11, which is:

```
(Compound 1, SEQ ID NO: 6)
Hy-H[Aib]EGSFTSELATILDEQAARDFIAWLIAHKITD-OH;

(Compound 2, SEQ ID NO: 7)
Hy-H[Aib]EGTFSSELATILDEQAARDFIAWLIAHKITD-OH;

(Compound 3, SEQ ID NO: 8)
Hy-H[Aib]EGTFTSELATILDEQAARDFIAWLIAHKITD-OH;

(Compound 4, SEQ ID NO: 9)
Hy-H[Aib]EGSFTSELATILDEQAARDFIAWLIEHKITD-OH;

(Compound 5, SEQ ID NO: 10)
Hy-H[Aib]EGTFTSELATILDEQAARDFIAWLIEHKITD-OH;

(Compound 6, SEQ ID NO: 11)
Hy-H[Aib]EGSFTSELATILDEQAARDFIAWLIHHKITD-OH;

(Compound 7, SEQ ID NO: 12)
Hy-H[Aib]EGSFTSELATILDEQAARDFIAWLIYHKITD-OH;

(Compound 8, SEQ ID NO: 13)
Hy-H[Aib]EGSFTSELATILDEQAARDFIAWLILHKITD-OH;

(Compound 9, SEQ ID NO: 14)
Hy-H[Aib]EGTFTDELATILDEQAARDFIAWLIAHKITD-OH;

(Compound 10, SEQ ID NO: 15)
Hy-H[Aib]EGTFTSELSTILDEQAARDFIAWLIAHKITD-OH;

(Compound 11, SEQ ID NO: 16)
Hy-H[Aib]EGTFTSELATILDGKAARDFIAWLIAHKITD-OH;

(Compound 13, SEQ ID NO: 18)
Hy-H[Aib]EGTFTSELATILDEQAARDFIAWLQAHKITD-OH;

(Compound 14, SEQ ID NO: 19)
Hy-H[Aib]EGTFTSELATILDEQAARDFIAWLYAHKITD-OH;

(Compound 19, SEQ ID NO: 24)
Hy-H[Aib]EGTFTSELATILDEQAARDFIAWLIAQKITD-OH;

(Compound 20, SEQ ID NO: 25)
Hy-H[Aib]EGTFTSELATILDEQAARDFIAWLIAYKITD-OH;

(Compound 23, SEQ ID NO: 28)
Hy-H[Aib]EGSFTSELATILDEQAARDFIAWLYEHKITD-OH;

(Compound 24, SEQ ID NO: 29)
Hy-H[Aib]EGSFTSELATILDEQAARDFIAWLQAHKITD-OH;

(Compound 25, SEQ ID NO: 30)
Hy-H[Aib]EGSFTSELATILDEQAARDFIAWLIAQKITD-OH;

(Compound 26, SEQ ID NO: 31)
Hy-H[Aib]EGTFTSELATILDEQAARDFIAWLQAQKITD-OH;

(Compound 28, SEQ ID NO: 33)
Hy-H[Aib]EGSFTSELATILDEQAARDFIAWLYAHKITD-OH;

(Compound 29, SEQ ID NO: 34)
Hy-H[Aib]EGTFTDELATILDEQAARDFIAWLQAQKITD-OH;

(Compound 31, SEQ ID NO: 36)
Hy-H[Aib]EGSFTSELATILDGKAARDFIAWLIAHKITD-OH;

(Compound 32, SEQ ID NO: 37)
Hy-H[Aib]EGTFSSELATILDGKAARDFIAWLIAHKITD-OH;

(Compound 33, SEQ ID NO: 38)
Hy-H[Aib]EGTFTSELATILDEQAARDFINWLIAHKITD-OH;

(Compound 34, SEQ ID NO: 39)
Hy-H[Aib]EGTFTSELATILDEQAARDFISWLIAHKITD-OH;

(Compound 35, SEQ ID NO: 40)
Hy-H[Aib]EGTFTSELATILDEQAARDFINWLKAHKITD-OH;
or (Compound 37, SEQ ID NO: 42)
Hy-H[Aib]EGTFTSELATILDEQAARDFINWLKEQKITD-OH.
```

13. The dual agonist or pharmaceutically acceptable salt thereof according to claim 1, wherein X28 is A and X29 is H.

14. The dual agonist or pharmaceutically acceptable salt thereof according to claim 1, wherein X28 is E and X29 is H.

15. The dual agonist or pharmaceutically acceptable salt thereof according to claim 1, wherein U is a peptide sequence of 3-7 lysine residues, and wherein the lysine residues in the peptide are all L-configuration or all D-configuration.

16. A composition comprising a dual agonist according to claim 1, or a pharmaceutically acceptable salt thereof, in admixture with a carrier and optionally further comprising excipient or vehicle, optionally wherein the carrier is a pharmaceutically acceptable carrier.

17. A method of increasing intestinal mass, improving intestinal function, increasing intestinal blood flow, or repairing intestinal damage or dysfunction in a subject in need thereof, the method comprising administering a dual agonist according to claim 1 to the subject.

18. A method of reducing weight gain, reducing gastric emptying or intestinal transit, reducing food intake, reducing appetite, or promoting weight loss in a subject in need thereof, the method comprising administering a dual agonist according to claim 1 to the subject.

19. A method of treating obesity, morbid obesity, obesity-linked gallbladder disease, obesity-induced sleep apnea, inadequate glucose control, glucose tolerance, dyslipidemia, diabetes, pre-diabetes, metabolic syndrome or hypertension in a subject in need thereof, the method comprising administering a dual agonist according to claim 1 to the subject.

\* \* \* \* \*

SEQUENCE LISTING

<160> NUMBER OF SEQ ID NOS: 76

<210> SEQ ID NO 1
<211> LENGTH: 33
<212> TYPE: PRT

<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K

```
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 3

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa

<210> SEQ ID NO 4
<211> LENGTH: 17
<212> TYPE: PRT
<213> ORGANISM: Artificial Sequence
<220> FEATURE:
<223> OTHER INFORMATION: GLP-1/GLP-2 Dual Agonist peptide

<400> SEQUENCE: 4

Ser Glu Leu Ala Thr Ile Leu Asp Glu Gln Ala Ala Arg Asp Phe Ile
1               5                   10                  15

Ala

<210> SEQ ID NO 5
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: misc
<222> LOCATION: (5)..(5)
<223> OTHER INFORMATION: Xaa is S or T
<220> FEATURE:
<221> NAME/KEY: misc
<222> LOCATION: (7)..(7)
<223> OTHER INFORMATION: Xaa is S or T
<220> FEATURE:
<221> NAME/KEY: misc
<222> LOCATION: (28)..(28)
<223> OTHER INFORMATION: Xaa is A, E, H, Y or L
<220> FEATURE:
<221> NAME/KEY: misc
<222> LOCATION: (29)..(29)
<223> OTHER INFORMATION: Xaa is H, Y or Q

<400> SEQUENCE: 5
```

His Xaa Glu Gly Xaa Phe Xaa Ser Glu Leu Ala Thr Ile Leu Asp Glu
1               5                   10                  15

Gln Ala Ala Arg Asp Phe Ile Ala Trp Leu Ile Xaa Xaa Lys Ile Thr
            20                  25                  30

Asp

<210> SEQ ID NO 6
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 6

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp

<210> SEQ ID NO 7
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 7

His Xaa Glu Gly Thr Phe Ser Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp

<210> SEQ ID NO 8
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 8

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp

<210> SEQ ID NO 9
<211> LENGTH: 33
<212> TYPE: PRT

```
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 9

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 10
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 10

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 11
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 11

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Ile His His Lys Ile Thr
            20                  25                  30

Asp

<210> SEQ ID NO 12
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 12

His Xaa Glu Gly Ser Phe Thr Ser Glu Leu Ala Thr Ile Leu Asp Glu
1               5                   10                  15
```

Gln Ala Ala Arg Asp Phe Ile Ala Trp Leu Ile Tyr His Lys Ile Thr
            20                  25                  30

Asp

<210> SEQ ID NO 13
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 13

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Ile Leu His Lys Ile Thr
            20                  25                  30

Asp

<210> SEQ ID NO 14
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 14

His Xaa Glu Gly Thr Phe Thr Asp Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp

<210> SEQ ID NO 15
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 15

His Xaa Glu Gly Thr Phe Thr Ser Glu Leu Ser Thr Ile Leu Asp Glu
1               5                   10                  15

Gln Ala Ala Arg Asp Phe Ile Ala Trp Leu Ile Ala His Lys Ile Thr
            20                  25                  30

Asp

<210> SEQ ID NO 16
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:

```
<221> NAME/KEY: MOD_RES
<222> LOCATION: (2)..(2)
<223> OTHER INFORMATION: Aib

<400> SEQUENCE: 16

His Xaa Glu Gly Thr Phe Thr Ser Glu Leu Ala Thr Ile Leu Asp Gly
1               5                   10                  15

Lys Ala Ala Arg Asp Phe Ile Ala Trp Leu Ile Ala His Lys Ile Thr
            20                  25                  30

Asp

<210> SEQ ID NO 17
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 17

His Xaa Glu Gly Thr Phe Thr Ser Glu Leu Ala Thr Ile Leu Asp Glu
1               5                   10                  15

Gln Ala Ala Arg Asp Phe Ile Ala Trp Leu His Ala His Lys Ile Thr
            20                  25                  30

Asp

<210> SEQ ID NO 18
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 18

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Gln Ala His Lys Ile Thr
            20                  25                  30

Asp

<210> SEQ ID NO 19
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 19

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Tyr Ala His Lys Ile Thr
            20                  25                  30

Asp
```

<210> SEQ ID NO 20
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 20

His Xaa Glu Gly Thr Phe Thr Ser Glu Leu Ala Thr Ile Leu Asp Glu
 1               5                  10                  15

Gln Ala Ala Arg Asp Phe Ile Ala Trp Leu Ile Gln His Lys Ile Thr
            20                  25                  30

Asp

<210> SEQ ID NO 21
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 21

His Xaa Glu Gly Thr Phe Thr Ser Glu Leu Ala Thr Ile Leu Asp Glu
 1               5                  10                  15

Gln Ala Ala Arg Asp Phe Ile Ala Trp Leu Ile Lys His Lys Ile Thr
            20                  25                  30

Asp

<210> SEQ ID NO 22
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 22

His Xaa Glu Gly Thr Phe Thr Ser Glu Leu Ala Thr Ile Leu Asp Glu
 1               5                  10                  15

Gln Ala Ala Arg Asp Phe Ile Ala Trp Leu Ile Arg His Lys Ile Thr
            20                  25                  30

Asp

<210> SEQ ID NO 23
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

```
<400> SEQUENCE: 23

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Ile Ser His Lys Ile Thr
            20                  25                  30

Asp

<210> SEQ ID NO 24
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 24

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Ile Ala Gln Lys Ile Thr
            20                  25                  30

Asp

<210> SEQ ID NO 25
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 25

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Ile Ala Tyr Lys Ile Thr
            20                  25                  30

Asp

<210> SEQ ID NO 26
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 26

His Xaa Glu Gly Thr Phe Thr Ser Glu Leu Ala Thr Ile Leu Asp Glu
1               5                   10                  15

Gln Ala Ala Arg Asp Phe Ile Ala Trp Leu His Gln His Lys Ile Thr
            20                  25                  30

Asp

<210> SEQ ID NO 27
<211> LENGTH: 33
```

```
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 27

His Xaa Glu Gly Ser Phe Thr Ser Glu Leu Ala Thr Ile Leu Asp Glu
1               5                   10                  15

Gln Ala Ala Arg Asp Phe Ile Ala Trp Leu His Ala His Lys Ile Thr
            20                  25                  30

Asp

<210> SEQ ID NO 28
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 28

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Tyr Glu His Lys Ile Thr
            20                  25                  30

Asp

<210> SEQ ID NO 29
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 29

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Gln Ala His Lys Ile Thr
            20                  25                  30

Asp

<210> SEQ ID NO 30
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 30

His Xaa Glu Gly Ser Phe Thr Ser Glu Leu Ala Thr Ile Leu Asp Glu
1               5                   10                  15
```

Gln Ala Ala Arg Asp Phe Ile Ala Trp Leu Ile Ala Gln Lys Ile Thr
            20                  25                  30

Asp

<210> SEQ ID NO 31
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 31

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Gln Ala Gln Lys Ile Thr
            20                  25                  30

Asp

<210> SEQ ID NO 32
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 32

His Xaa Glu Gly Thr Phe Thr Ser Glu Leu Ser Thr Ile Leu Asp Glu
1               5                   10                  15

Gln Ala Ala Arg Asp Phe Ile Ala Trp Leu His Ala Gln Lys Ile Thr
            20                  25                  30

Asp

<210> SEQ ID NO 33
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 33

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Tyr Ala His Lys Ile Thr
            20                  25                  30

Asp

<210> SEQ ID NO 34
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide

```
<220> FEATURE:
<221> NAME/KEY: MOD_RES
<222> LOCATION: (2)..(2)
<223> OTHER INFORMATION: Aib

<400> SEQUENCE: 34

His Xaa Glu Gly Thr Phe Thr Asp Glu Leu Ala Thr Ile Leu Asp Glu
1               5                   10                  15

Gln Ala Ala Arg Asp Phe Ile Ala Trp Leu Gln Ala Gln Lys Ile Thr
            20                  25                  30

Asp

<210> SEQ ID NO 35
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 35

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Tyr Arg His Lys Ile Thr
            20                  25                  30

Asp

<210> SEQ ID NO 36
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 36

His Xaa Glu Gly Ser Phe Thr Ser Glu Leu Ala Thr Ile Leu Asp Gly
1               5                   10                  15

Lys Ala Ala Arg Asp Phe Ile Ala Trp Leu Ile Ala His Lys Ile Thr
            20                  25                  30

Asp

<210> SEQ ID NO 37
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 37

His Xaa Glu Gly Thr Phe Ser Ser Glu Leu Ala Thr Ile Leu Asp Gly
1               5                   10                  15

Lys Ala Ala Arg Asp Phe Ile Ala Trp Leu Ile Ala His Lys Ile Thr
            20                  25                  30
```

Asp

<210> SEQ ID NO 38
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 38

His Xaa Glu Gly Thr Phe Thr Ser Glu Leu Ala Thr Ile Leu Asp Glu
1               5                   10                  15

Gln Ala Ala Arg Asp Phe Ile Asn Trp Leu Ile Ala His Lys Ile Thr
            20                  25                  30

Asp

<210> SEQ ID NO 39
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 39

His Xaa Glu Gly Thr Phe Thr Ser Glu Leu Ala Thr Ile Leu Asp Glu
1               5                   10                  15

Gln Ala Ala Arg Asp Phe Ile Ser Trp Leu Ile Ala His Lys Ile Thr
            20                  25                  30

Asp

<210> SEQ ID NO 40
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 40

His Xaa Glu Gly Thr Phe Thr Ser Glu Leu Ala Thr Ile Leu Asp Glu
1               5                   10                  15

Gln Ala Ala Arg Asp Phe Ile Asn Trp Leu Lys Ala His Lys Ile Thr
            20                  25                  30

Asp

<210> SEQ ID NO 41
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

```
<400> SEQUENCE: 41

His Xaa Glu Gly Thr Phe Thr Ser Glu Leu Ala Thr Ile Leu Asp Glu
1               5                   10                  15

Gln Ala Ala Arg Asp Phe Ile Asn Trp Leu Lys Ser Tyr Lys Ile Thr
            20                  25                  30

Asp

<210> SEQ ID NO 42
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 42

His Xaa Glu Gly Thr Phe Thr Ser Glu Leu Ala Thr Ile Leu Asp Glu
1               5                   10                  15

Gln Ala Ala Arg Asp Phe Ile Asn Trp Leu Lys Glu Gln Lys Ile Thr
            20                  25                  30

Asp

<210> SEQ ID NO 43
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide

<400> SEQUENCE: 43

His Gly Glu Gly Thr Phe Thr Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp

<210> SEQ ID NO 44
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 44

His Xaa Glu Gly Thr Phe Ser Ser Glu Leu Ser Thr Ile Leu Glu Glu
1               5                   10                  15

Gln Ala Ser Arg Glu Phe Ile Ala Trp Leu Ile Ala His Lys Ile Thr
            20                  25                  30

Glu

<210> SEQ ID NO 45
<211> LENGTH: 33
<212> TYPE: PRT
<213> ORGANISM: Artificial Sequence
<220> FEATURE:
```

-continued

<223> OTHER INFORMATION: GLP-1/GLP-2 Dual Agonist peptide

<400> SEQUENCE: 45

His Gly Glu Gly Ser Phe Ser Ser Glu Leu Ala Thr Ile Leu Asp Glu
1               5                   10                  15

Gln Ala Ala Arg Asp Phe Ile Ala Trp Leu Ile Gln His Lys Ile Thr
            20                  25                  30

Asp

<210> SEQ ID NO 46
<211> LENGTH: 33
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MOD_RES
<222> LOCATION: (2)..(2)
<223> OTHER INFORMATION: Aib

<400> SEQUENCE: 46

His Xaa Glu Gly Ser Phe Ser Ser Glu Leu Ala Thr Ile Leu Asp Glu
1               5                   10                  15

Gln Ala Ala Arg Asp Phe Ile Ala Trp Leu Ile Gln His Lys Ile Thr
            20                  25                  30

Asp

<210> SEQ ID NO 47
<211> LENGTH: 34
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K

```
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 47

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys

<210> SEQ ID NO 48
<211> LENGTH: 35
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
```

```
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 48

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys Lys
        35

<210> SEQ ID NO 49
<211> LENGTH: 36
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
```

```
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 49

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys Lys Lys
        35

<210> SEQ ID NO 50
<211> LENGTH: 37
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
```

```
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 50

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys Lys Lys Lys
        35

<210> SEQ ID NO 51
<211> LENGTH: 38
<212> TYPE: PRT
<213> ORGANISM: Artificial Sequence
<220> FEATURE:
```

```
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 51

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30
```

Xaa Lys Lys Lys Lys Lys
        35

<210> SEQ ID NO 52
<211> LENGTH: 39
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 52

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys Lys Lys Lys Lys Lys
        35

<210> SEQ ID NO 53
<211> LENGTH: 40
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K

```
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 53

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys Lys Lys Lys Lys Lys Lys
        35                  40

<210> SEQ ID NO 54
<211> LENGTH: 41
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
```

```
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 54

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
                20                  25                  30

Xaa Lys Lys Lys Lys Lys Lys Lys Lys
        35                  40

<210> SEQ ID NO 55
<211> LENGTH: 42
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
```

```
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 55

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys Lys Lys Lys Lys Lys Lys Lys Lys
        35                  40

<210> SEQ ID NO 56
<211> LENGTH: 43
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
```

```
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 56

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys Lys Lys Lys Lys Lys Lys Lys Lys
        35                  40

<210> SEQ ID NO 57
<211> LENGTH: 44
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
```

```
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 57

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys Lys Lys Lys Lys Lys Lys Lys Lys Lys
        35                  40

<210> SEQ ID NO 58
<211> LENGTH: 45
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
``` at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 58

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
                20                  25                  30

Xaa Lys Lys Lys Lys Lys Lys Lys Lys Lys Lys Lys Lys
        35                  40                  45

<210> SEQ ID NO 59
<211> LENGTH: 46
<212> TYPE: PRT
<213> ORGANISM: Artificial Sequence -continued

```
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 59

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
```

```
                20                  25                  30
Xaa Lys Lys Lys Lys Lys Lys Lys Lys Lys Lys Lys Lys
        35                  40                  45

<210> SEQ ID NO 60
<211> LENGTH: 47
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
```

```
<221> NAME/KEY: MISC_FEATURE
<222> LOCATION: (33)..(33)
<223> OTHER INFORMATION: Xaa is D or E

<400> SEQUENCE: 60

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys Lys Lys Lys Lys Lys Lys Lys Lys Lys Lys Lys
        35                  40                  45

<210> SEQ ID NO 61
<211> LENGTH: 48
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
```

<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E

<400> SEQUENCE: 61

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Lys Lys Lys Lys Lys Lys Lys Lys Lys Lys Lys Lys Lys
        35                  40                  45

<210> SEQ ID NO 62
<211> LENGTH: 34
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:

```
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(34)
<223> OTHER INFORMATION: Xaa is D-lysine

<400> SEQUENCE: 62

His Xaa Glu Gly Xaa Phe Xaa Xaa Glu Xaa Xaa Thr Ile Leu Xaa Xaa
 1               5                  10                  15

Xaa Ala Xaa Xaa Xaa Phe Ile Xaa Trp Leu Xaa Xaa Xaa Lys Ile Thr
            20                  25                  30

Xaa Xaa

<210> SEQ ID NO 63
<211> LENGTH: 35
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
```

```
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(35)
<223> OTHER INFORMATION: Xaa is D-lysine

<400> SEQUENCE: 63

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa
        35

<210> SEQ ID NO 64
<211> LENGTH: 36
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
```

```
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(36)
<223> OTHER INFORMATION: Xaa is D-lysine

<400> SEQUENCE: 64

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa Xaa
        35

<210> SEQ ID NO 65
<211> LENGTH: 37
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
```

```
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(37)
<223> OTHER INFORMATION: Xaa is D-lysine

<400> SEQUENCE: 65

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
                20                  25                  30

Xaa Xaa Xaa Xaa Xaa
            35
```

```
<210> SEQ ID NO 66
<211> LENGTH: 38
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
```

<221> NAME/KEY: MISC_FEATURE
<222> LOCATION: (34)..(38)
<223> OTHER INFORMATION: Xaa is D-lysine

<400> SEQUENCE: 66

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa Xaa Xaa Xaa
        35

<210> SEQ ID NO 67
<211> LENGTH: 39
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)

```
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(39)
<223> OTHER INFORMATION: Xaa is D-lysine

<400> SEQUENCE: 67

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa Xaa Xaa Xaa Xaa
        35

<210> SEQ ID NO 68
<211> LENGTH: 40
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
```

```
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(40)
<223> OTHER INFORMATION: Xaa is D-lysine

<400> SEQUENCE: 68

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa Xaa Xaa Xaa Xaa Xaa
        35                  40

<210> SEQ ID NO 69
<211> LENGTH: 41
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
```

```
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(41)
<223> OTHER INFORMATION: Xaa is D-lysine

<400> SEQUENCE: 69

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
                20                  25                  30

Xaa Xaa Xaa Xaa Xaa Xaa Xaa Xaa Xaa
            35                  40

<210> SEQ ID NO 70
<211> LENGTH: 42
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
```

```
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(42)
<223> OTHER INFORMATION: Xaa is D-lysine

<400> SEQUENCE: 70

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa Xaa Xaa Xaa Xaa Xaa Xaa Xaa
        35                  40

<210> SEQ ID NO 71
<211> LENGTH: 43
<212> TYPE: PRT
<213> ORGANISM: Artificial Sequence
<220> FEATURE:
<223> OTHER INFORMATION: GLP-1/GLP-2 Dual Agonist peptide
<220> FEATURE:
```

```
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(43)
<223> OTHER INFORMATION: Xaa is D-lysine

<400> SEQUENCE: 71

His Xaa Glu Gly Xaa Phe Xaa Xaa Glu Xaa Xaa Thr Ile Leu Xaa Xaa
1               5                   10                  15
```

```
Xaa Ala Xaa Xaa Xaa Phe Ile Xaa Trp Leu Xaa Xaa Xaa Lys Ile Thr
             20                  25                  30

Xaa Xaa Xaa Xaa Xaa Xaa Xaa Xaa Xaa Xaa Xaa
         35                  40
```

<210> SEQ ID NO 72
<211> LENGTH: 44
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q

```
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(44)
<223> OTHER INFORMATION: Xaa is D-lysine

<400> SEQUENCE: 72

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa Xaa Xaa Xaa Xaa Xaa Xaa Xaa Xaa Xaa
        35                  40

<210> SEQ ID NO 73
<211> LENGTH: 45
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
```

```
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(45)
<223> OTHER INFORMATION: Xaa is D-lysine

<400> SEQUENCE: 73

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa Xaa Xaa Xaa Xaa Xaa Xaa Xaa Xaa Xaa Xaa
        35                  40                  45

<210> SEQ ID NO 74
<211> LENGTH: 46
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
     at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
     at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
```

```
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(46)
<223> OTHER INFORMATION: Xaa is D-lysine

<400> SEQUENCE: 74

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa Xaa Xaa Xaa Xaa Xaa Xaa Xaa Xaa Xaa Xaa Xaa
        35                  40                  45

<210> SEQ ID NO 75
<211> LENGTH: 47
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
```

```
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(47)
<223> OTHER INFORMATION: Xaa is D-lysine

<400> SEQUENCE: 75

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa Xaa Xaa Xaa Xaa Xaa Xaa Xaa Xaa Xaa Xaa Xaa Xaa
        35                  40                  45

<210> SEQ ID NO 76
<211> LENGTH: 48
<212> TYPE: PRT
<213> ORGANISM: Artificial Sequence
<220> FEATURE:
<223> OTHER INFORMATION: GLP-1/GLP-2 Dual Agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is S or T; When Xaa at position 5 is S, Xaa
      at position 7 must be T.
<220> FEATURE:
```

```
<221> NAME/KEY: MISC_FEATURE
<222> LOCATION: (7)..(7)
<223> OTHER INFORMATION: Xaa is S or T; When Xaa at position 7 is S, Xaa
      at position 5 must be T.
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M or V
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is E, A or G
<220> FEATURE:
<221> NAME/KEY: MISC_FEATURE
<222> LOCATION: (17)..(17)
<223> OTHER INFORMATION: Xaa is Q, E, L or K
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R or K
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or S
<220> FEATURE:
<221> NAME/KEY: MISC_FEATURE
<222> LOCATION: (27)..(27)
<223> OTHER INFORMATION: Xaa is I, Y, Q, H or K
<220> FEATURE:
<221> NAME/KEY: MISC_FEATURE
<222> LOCATION: (28)..(28)
<223> OTHER INFORMATION: Xaa is A, E, H, Y, L, K, Q, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(48)
<223> OTHER INFORMATION: Xaa is D-lysine

<400> SEQUENCE: 76

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa Xaa Xaa Xaa Xaa Xaa Xaa Xaa Xaa Xaa Xaa Xaa Xaa Xaa Xaa Xaa
        35                  40                  45
```